United States Patent
Jackson

(10) Patent No.: US 9,050,139 B2
(45) Date of Patent: Jun. 9, 2015

(54) ORTHOPEDIC IMPLANT ROD REDUCTION TOOL SET AND METHOD

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

(21) Appl. No.: 13/815,933

(22) Filed: Mar. 15, 2013

(65) Prior Publication Data

US 2013/0253598 A1 Sep. 26, 2013

Related U.S. Application Data

(60) Continuation-in-part of application No. 13/374,932, filed on Jan. 24, 2012, now Pat. No. 8,377,067, which is a continuation of application No. 12/584,413, filed on Sep. 4, 2009, now Pat. No. 8,100,915, which is a continuation of application No. 12/220,185, filed on Jul. 22, 2008, now Pat. No. 8,162,948, which is a division of application No. 11/502,926, filed on Aug. 11, 2006, now abandoned, which is a division of application No. 10/789,149, filed on Feb. 27, 2004, now Pat. No. 7,160,300, application No. 13/815,933, which is a continuation-in-part of application No. 11/272,508, filed on Nov. 10, 2005, and a continuation of application No. 10/966,289, filed on Nov. 23, 2004, now Pat. No. 8,152,810, which is a continuation-in-part of application No. 10/789,149, filed on Feb. 27, 2004, now Pat. No. 7,160,300.

(60) Provisional application No. 60/630,536, filed on Nov. 23, 2004.

(51) Int. Cl.
A61B 17/70 (2006.01)
A61B 17/56 (2006.01)

(52) U.S. Cl.
CPC ........ *A61B 17/7001* (2013.01); *A61B 17/7011* (2013.01); *A61B 17/7032* (2013.01); *A61B 17/7037* (2013.01); *A61B 17/7085* (2013.01); *A61B 17/7091* (2013.01); *A61B 17/7088* (2013.01); *A61B 2017/564* (2013.01)

(58) Field of Classification Search
CPC .......... A61B 17/7032; A61B 17/7088; A61B 17/7085; A61B 17/7091; A61B 17/7037; A61B 17/7011
USPC ...... 606/246, 86 A, 86 R, 279, 264, 301–309, 606/261, 259
See application file for complete search history.

(56) References Cited

U.S. PATENT DOCUMENTS

| | | |
|---|---|---|
| 854,956 A | 5/1907 | Martin |
| 1,472,464 A | 10/1923 | Ellison |

(Continued)

FOREIGN PATENT DOCUMENTS

| | | |
|---|---|---|
| AU | 2012203959 | 8/2012 |
| CA | 2577436 | 6/2006 |

(Continued)

OTHER PUBLICATIONS

Brochure of SofamorDanek the Spine Specialist, TSRH, Pedicle Screw Spinal System, Publication Date: Jan. 23, 1995.

(Continued)

*Primary Examiner* — Pedro Philogene
(74) *Attorney, Agent, or Firm* — John C. McMahon

(57) ABSTRACT

A tool set for implanting a rod in a human spine in conjunction with bone screws.

1 Claim, 17 Drawing Sheets

(56) References Cited

U.S. PATENT DOCUMENTS

| | | |
|---|---|---|
| 2,243,717 A | 5/1941 | Moreira |
| 2,346,346 A | 4/1944 | Anderson |
| 2,362,999 A | 11/1944 | Elmer |
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 3,997,138 A | 12/1976 | Crock et al. |
| 4,033,139 A | 7/1977 | Frederick |
| 4,041,939 A | 8/1977 | Hall |
| 4,190,091 A | 2/1980 | Colognori |
| 4,347,845 A | 9/1982 | Mayfield |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,838,264 A | 6/1989 | Bremer et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,015,247 A | 5/1991 | Michelson |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Baker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |

(56) References Cited

U.S. PATENT DOCUMENTS

| | | |
|---|---|---|
| 5,855,151 A | 1/1999 | Habermehl |
| 5,863,293 A | 1/1999 | Richelsoph |
| 5,865,487 A | 2/1999 | Gore et al. |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,088 A | 5/2000 | Winslow |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,189,422 B1 | 2/2001 | Stihl |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,379,356 B1 | 4/2002 | Jackson |
| 6,402,752 B2 | 6/2002 | Schaffler-Wachter et al. |
| 6,402,757 B1 | 6/2002 | Moore, III et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,798 B1 | 11/2002 | Howland |
| 6,478,800 B1 | 11/2002 | Fraser et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,602,255 B1 | 8/2003 | Campbell et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,484 B2 | 9/2003 | Betz |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |

(56) References Cited

U.S. PATENT DOCUMENTS

| | | |
|---|---|---|
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,248 B2 | 3/2004 | Jackson |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,687 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Bieeermann et al. |
| 6,740,086 B2 | 5/2004 | Richelsoph |
| 6,740,089 B2 | 5/2004 | Haider |
| 6,743,231 B1 | 6/2004 | Gray |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,719 B2 | 7/2004 | Justis et al. |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,835,205 B2 | 12/2004 | Atkinson et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,044,947 B2 | 5/2006 | de la Torre et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann, et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,250,052 B2 | 7/2007 | Landry et al. |
| 7,264,621 B2 | 9/2007 | Coates et al. |
| 7,270,665 B2 | 9/2007 | Morrison et al. |
| 7,282,064 B2 | 10/2007 | Chin |
| 7,290,347 B2 | 11/2007 | Augostino |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,377,922 B2 | 5/2008 | Barker |
| 7,445,627 B2 | 11/2008 | Hawkes et al. |
| 7,465,306 B2 | 12/2008 | Pond |
| 7,470,279 B2 | 12/2008 | Jackson |
| 7,476,228 B2 | 1/2009 | Abdou |
| 7,476,238 B2 | 1/2009 | Panjabi |
| 7,479,156 B2 | 1/2009 | Lourdel et al. |
| 7,491,208 B2 | 2/2009 | Pond, Jr. et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,638 B2 | 5/2009 | Anderson et al. |
| 7,527,640 B2 | 5/2009 | Ziolo et al. |
| 7,530,992 B2 | 5/2009 | Biedermann et al. |
| 7,556,639 B2 | 7/2009 | Rothman et al. |
| 7,559,942 B2 | 7/2009 | Paul et al. |
| 7,559,943 B2 | 7/2009 | Mujwid |
| 7,563,264 B2 | 7/2009 | Landry et al. |

(56) References Cited

U.S. PATENT DOCUMENTS

| | | |
|---|---|---|
| 7,563,274 B2 | 7/2009 | Justis et al. |
| 7,563,275 B2 | 7/2009 | Falahee et al. |
| 7,563,283 B2 | 7/2009 | Kwak |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,589 B2 | 9/2009 | Falahee |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,601,171 B2 | 10/2009 | Ainsworth |
| 7,604,653 B2 | 10/2009 | Kitchen |
| 7,604,654 B2 | 10/2009 | Fallin et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,618,442 B2 | 11/2009 | Spitler et al. |
| 7,618,443 B2 | 11/2009 | Abdou |
| 7,621,912 B2 | 11/2009 | Harms et al. |
| 7,621,918 B2 | 11/2009 | Jackson |
| 7,621,940 B2 | 11/2009 | Harms et al. |
| 7,621,941 B2 | 11/2009 | Schlapfer et al. |
| 7,625,393 B2 | 12/2009 | Fallin et al. |
| 7,625,394 B2 | 12/2009 | Molz, IV et al. |
| 7,632,292 B2 | 12/2009 | Sengupta et al. |
| 7,641,673 B2 | 1/2010 | Le Couedic et al. |
| 7,641,674 B2 | 1/2010 | Young |
| 7,645,294 B2 | 1/2010 | Kalfas et al. |
| 7,648,522 B2 | 1/2010 | David |
| 7,651,502 B2 | 1/2010 | Jackson |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,666,188 B2 | 2/2010 | Anderson et al. |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,375 B2 | 3/2010 | Ritland |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,475 B2 | 4/2010 | Justis et al. |
| 7,695,496 B2 | 4/2010 | Labrom et al. |
| 7,695,497 B2 | 4/2010 | Cordaro et al. |
| 7,695,498 B2 | 4/2010 | Ritland |
| 7,695,514 B2 | 4/2010 | Kwak |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,260 B2 | 6/2010 | Albert et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,233 B2 | 7/2010 | Farr et al. |
| 7,749,258 B2 | 7/2010 | Biedermann et al. |
| 7,758,618 B2 | 7/2010 | Walder et al. |
| 7,763,052 B2 | 7/2010 | Jahng |
| 7,763,057 B2 | 7/2010 | Abdelgany et al. |
| 7,766,915 B2 | 8/2010 | Jackson |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,067 B2 | 8/2010 | Jackson |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,815,665 B2 | 10/2010 | Jahng et al. |
| 7,819,902 B2 | 10/2010 | Abdelgany et al. |
| 7,824,430 B2 | 11/2010 | Allard et al. |
| 7,833,250 B2 | 11/2010 | Jackson |
| 7,833,252 B2 | 11/2010 | Justis et al. |
| 7,846,190 B2 | 12/2010 | Ball |
| 7,850,715 B2 | 12/2010 | Banouskou et al. |
| 7,862,587 B2 | 1/2011 | Jackson |
| 7,862,588 B2 | 1/2011 | Abdou |
| 7,887,539 B2 | 2/2011 | Dunbar, Jr. et al. |
| 7,896,902 B2 | 3/2011 | Jeon et al. |
| 7,901,436 B2 | 3/2011 | Baccelli |
| 7,901,437 B2 | 3/2011 | Jackson |
| 7,909,830 B2 | 3/2011 | Frigg et al. |
| 7,947,064 B2 | 5/2011 | Bergeron et al. |
| 7,951,170 B2 | 5/2011 | Jackson |
| 7,955,358 B2 | 6/2011 | Albert |
| 7,967,848 B2 | 6/2011 | Abdelgany |
| 7,988,694 B2 | 8/2011 | Barrus et al. |
| 8,034,083 B2 | 10/2011 | Abdelgany et al. |
| 8,055,487 B2 | 11/2011 | James |
| 8,062,340 B2 | 11/2011 | Berrevoets et al. |
| 8,066,739 B2 | 11/2011 | Jackson |
| 8,075,599 B2 | 12/2011 | Johnson et al. |
| 8,083,776 B2 | 12/2011 | Alvarez |
| 8,152,837 B2 | 4/2012 | Altarac et al. |
| 8,172,876 B2 | 5/2012 | Janowski et al. |
| 8,197,517 B1 | 6/2012 | Lab et al. |
| 8,211,110 B1 | 7/2012 | Corin et al. |
| 8,226,690 B2 | 7/2012 | Altarac et al. |
| 8,267,969 B2 | 9/2012 | Altarac et al. |
| 8,292,926 B2 | 10/2012 | Jackson |
| 8,292,934 B2 | 10/2012 | Justis et al. |
| 8,292,958 B1 | 10/2012 | Bruffey et al. |
| 8,343,165 B2 | 1/2013 | Berrevoets |
| 8,377,100 B2 | 2/2013 | Jackson |
| 8,377,101 B2 | 2/2013 | Barrus et al. |
| 8,388,659 B1 | 3/2013 | Lab et al. |
| 8,398,683 B2 | 3/2013 | Berrevoets et al. |
| 8,409,256 B2 | 4/2013 | Arnold et al. |
| 8,439,924 B1 | 5/2013 | McBride et al. |
| 8,475,498 B2 | 7/2013 | Jackson |
| 2001/0001119 A1 | 5/2001 | Lombardo |
| 2001/0007941 A1 | 7/2001 | Steiner et al. |
| 2001/0010000 A1 | 7/2001 | Gertzbein |
| 2001/0012937 A1 | 8/2001 | Schaffler et al. |
| 2001/0023350 A1 | 9/2001 | Choi |
| 2001/0025553 A1 | 10/2001 | Oesterle et al. |
| 2001/0027318 A1 | 10/2001 | Oribe et al. |
| 2001/0029375 A1 | 10/2001 | Betz |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |

(56) References Cited

U.S. PATENT DOCUMENTS

| | | |
|---|---|---|
| 2002/0029040 A1 | 3/2002 | Morrison et al. |
| 2002/0035360 A1 | 3/2002 | Connors et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0045904 A1 | 4/2002 | Fuss et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0058950 A1 | 5/2002 | Winterbottom et al. |
| 2002/0068941 A1 | 6/2002 | Hanson et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0082603 A1 | 6/2002 | Dixon et al. |
| 2002/0087159 A1 | 7/2002 | Thomas et al. |
| 2002/0087161 A1 | 7/2002 | Randall et al. |
| 2002/0091386 A1 | 7/2002 | Martin et al. |
| 2002/0091390 A1 | 7/2002 | Michelson |
| 2002/0095153 A1 | 7/2002 | Jones et al. |
| 2002/0103487 A1 | 8/2002 | Errico et al. |
| 2002/0111626 A1 | 8/2002 | Ralph et al. |
| 2002/0111628 A1 | 8/2002 | Ralph et al. |
| 2002/0116001 A1 | 8/2002 | Schafer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173789 A1 | 11/2002 | Howland |
| 2002/0173791 A1 | 11/2002 | Howland |
| 2002/0193795 A1 | 12/2002 | Gertzbein et al. |
| 2002/0198526 A1 | 12/2002 | Shaolian et al. |
| 2003/0004519 A1 | 1/2003 | Torode et al. |
| 2003/0023240 A1 | 1/2003 | Amrein et al. |
| 2003/0023243 A1 | 1/2003 | Biedermann et al. |
| 2003/0055426 A1 | 3/2003 | Carbone et al. |
| 2003/0060826 A1 | 3/2003 | Foley et al. |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0149432 A1 | 8/2003 | Frigg et al. |
| 2003/0150897 A1 | 8/2003 | Ng |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |
| 2003/0176863 A1 | 9/2003 | Ueyama et al. |
| 2003/0181913 A1 | 9/2003 | Liebermann |
| 2003/0191469 A1 | 10/2003 | Ralph et al. |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0199874 A1 | 10/2003 | Michelson |
| 2003/0026529 A1 | 11/2003 | Shluzas |
| 2003/0208203 A1 | 11/2003 | Lim et al. |
| 2003/0208204 A1 | 11/2003 | Bailey et al. |
| 2003/0208275 A1 | 11/2003 | Michelson |
| 2003/0212398 A1 | 11/2003 | Jackson |
| 2003/0216735 A1 | 11/2003 | Altarac et al. |
| 2003/0216748 A1 | 11/2003 | Gitis et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas |
| 2004/0002708 A1 | 1/2004 | Ritland |
| 2004/0006342 A1 | 1/2004 | Altarac et al. |
| 2004/0034351 A1 | 2/2004 | Sherman et al. |
| 2004/0039384 A1 | 2/2004 | Boehm |
| 2004/0039385 A1 | 2/2004 | Mazda et al. |
| 2004/0044335 A1 | 3/2004 | de la Torre et al. |
| 2004/0049189 A1 | 3/2004 | Le Couudic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1* | 5/2004 | Lourdel et al. .................. 606/61 |
| 2004/0106925 A1 | 6/2004 | Culbert |
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0215190 A1 | 10/2004 | Nguyen et al. |
| 2004/0215191 A1 | 10/2004 | Kitchen |
| 2004/0220567 A1 | 11/2004 | Eisermann |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0267260 A1 | 12/2004 | Mack et al. |

(56) References Cited

U.S. PATENT DOCUMENTS

| | | |
|---|---|---|
| 2004/0267264 A1 | 12/2004 | Konieczynski et al. |
| 2005/0010219 A1 | 1/2005 | Dalton |
| 2005/0015439 A1 | 1/2005 | Balaji et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0137593 A1 | 6/2005 | Gray et al. |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0177154 A1 | 8/2005 | Moumene et al. |
| 2005/0177157 A1 | 8/2005 | Jahng |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0192589 A1 | 9/2005 | Raymond |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0267577 A1 | 12/2005 | Trieu |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran |
| 2006/0036242 A1* | 2/2006 | Nilsson et al. .................. 606/61 |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036255 A1 | 2/2006 | Pond |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |

(56) References Cited

U.S. PATENT DOCUMENTS

| | | |
|---|---|---|
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0106394 A1 | 5/2006 | Colleran |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0149251 A1 | 7/2006 | Ziolo et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1* | 8/2006 | Spitler et al. ............... 606/61 |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200023 A1 | 9/2006 | Melkent et al. |
| 2006/0200128 A1 | 9/2006 | Mueller |
| 2006/0200130 A1 | 9/2006 | Hawkins et al. |
| 2006/0200131 A1* | 9/2006 | Chao et al. ............... 606/61 |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247658 A1 | 11/2006 | Pond et al. |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Li et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2006/0293693 A1 | 12/2006 | Farr et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0032123 A1 | 2/2007 | Timm et al. |
| 2007/0043355 A1 | 2/2007 | Bette et al. |
| 2007/0043356 A1 | 2/2007 | Timm |
| 2007/0043357 A1 | 2/2007 | Kirschman |

(56) References Cited

U.S. PATENT DOCUMENTS

| | | |
|---|---|---|
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073294 A1 | 3/2007 | Chin et al. |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0124249 A1 | 5/2007 | Lim et al. |
| 2007/0129729 A1 | 6/2007 | Petit et al. |
| 2007/0135815 A1 | 6/2007 | Gerbec et al. |
| 2007/0156142 A1 | 7/2007 | Rezach et al. |
| 2007/0156237 A1 | 7/2007 | Kwak |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0250061 A1 | 10/2007 | Chin et al. |
| 2007/0260243 A1 | 11/2007 | Kagami |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0270869 A1 | 11/2007 | Young et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |

(56) References Cited

U.S. PATENT DOCUMENTS

| | | |
|---|---|---|
| 2008/0071277 A1 | 3/2008 | Warnick |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1* | 4/2008 | Biedermann et al. ............ 606/61 |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114403 A1 | 5/2008 | Kuester et al. |
| 2008/0119849 A1 | 5/2008 | Beardsley et al. |
| 2008/0119850 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154279 A1 | 6/2008 | Schumacher et al. |
| 2008/0154307 A1 | 6/2008 | Colleran et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0177332 A1 | 7/2008 | Reiley et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228184 A1 | 9/2008 | Hestad |
| 2008/0228227 A1 | 9/2008 | Brown et al. |
| 2008/0228228 A1 | 9/2008 | Hestad et al. |
| 2008/0228229 A1 | 9/2008 | Walder et al. |
| 2008/0234691 A1 | 9/2008 | Schwab |
| 2008/0234734 A1 | 9/2008 | Wabler et al. |
| 2008/0234736 A1 | 9/2008 | Trieu et al. |
| 2008/0234737 A1 | 9/2008 | Bosehert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0234756 A1 | 9/2008 | Sutcliffe et al. |
| 2008/0234759 A1 | 9/2008 | Marino |
| 2008/0243052 A1 | 10/2008 | Pond et al. |
| 2008/0243185 A1 | 10/2008 | Felix et al. |
| 2008/0243188 A1 | 10/2008 | Walder |
| 2008/0243194 A1 | 10/2008 | Lotz et al. |
| 2008/0249570 A1 | 10/2008 | Carson et al. |
| 2008/0249576 A1 | 10/2008 | Wawkes et al. |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0300630 A1 | 12/2008 | Bohnema et al. |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312655 A1 | 12/2008 | Kirschman et al. |
| 2008/0312692 A1 | 12/2008 | Brennan et al. |
| 2008/0312694 A1 | 12/2008 | Peterman et al. |
| 2008/0312696 A1 | 12/2008 | Batters et al. |
| 2008/0312701 A1 | 12/2008 | Batters et al. |
| 2008/0312703 A1 | 12/2008 | Hestad et al. |
| 2008/0312704 A1 | 12/2008 | Hestad et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0005817 A1 | 1/2009 | Friedrich et al. |
| 2009/0012567 A1 | 1/2009 | Biedermann et al. |
| 2009/0018583 A1 | 1/2009 | Song et al. |
| 2009/0018591 A1 | 1/2009 | Hawkes et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1* | 1/2009 | Hestad et al. .................. 606/254 |
| 2009/0030465 A1 | 1/2009 | Altarac et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0054932 A1 | 2/2009 | Butler et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099599 A1 | 4/2009 | Biedermann et al. |
| 2009/0099606 A1 | 4/2009 | Hestad et al. |
| 2009/0099607 A1 | 4/2009 | Fallin et al. |
| 2009/0099608 A1 | 4/2009 | Szczesny |

(56) References Cited

U.S. PATENT DOCUMENTS

| | | |
|---|---|---|
| 2009/0105760 A1 | 4/2009 | Frey |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0118772 A1 | 5/2009 | Diederich et al. |
| 2009/0125063 A1 | 5/2009 | Panjabi |
| 2009/0131981 A1 | 5/2009 | White |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0143829 A1 | 6/2009 | Shluzas |
| 2009/0149885 A1 | 6/2009 | Durwood et al. |
| 2009/0149887 A1 | 6/2009 | Schlaepfer et al. |
| 2009/0149892 A1 | 6/2009 | Stad et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2009/0326587 A1 | 12/2009 | Matthis et al. |
| 2010/0004692 A1 | 1/2010 | Biedermann et al. |
| 2010/0004695 A1 | 1/2010 | Stad et al. |
| 2010/0010540 A1 | 1/2010 | Park |
| 2010/0010544 A1 | 1/2010 | Fallin et al. |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030272 A1 | 2/2010 | Winslow |
| 2010/0030283 A1 | 2/2010 | King et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063550 A1 | 3/2010 | Felix et al. |
| 2010/0063551 A1 | 3/2010 | Richelsoph |
| 2010/0063552 A1 | 3/2010 | Chin et al. |
| 2010/0063553 A1 | 3/2010 | Warnick |
| 2010/0069919 A1 | 3/2010 | Carls et al. |
| 2010/0069963 A1 | 3/2010 | Eckman |
| 2010/0069964 A1 | 3/2010 | Lechmann |
| 2010/0069969 A1 | 3/2010 | Ampuero et al. |
| 2010/0087858 A1 | 4/2010 | Abdou |
| 2010/0087861 A1 | 4/2010 | Lechmann et al. |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0088782 A1 | 4/2010 | Oswald et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114108 A1 | 5/2010 | Strauss |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121385 A1 | 5/2010 | Blain et al. |
| 2010/0121386 A1 | 5/2010 | Peultier et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |

(56) References Cited

U.S. PATENT DOCUMENTS

| | | | |
|---|---|---|---|
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0204736 A1 | 8/2010 | Biedermann et al. |
| 2010/0222822 A1 | 9/2010 | Farris et al. |
| 2010/0222828 A1 | 9/2010 | Stad et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262196 A1 | 10/2010 | Barrus et al. |
| 2011/0004256 A1 | 1/2011 | Biedermann et al. |
| 2011/0046683 A1 | 2/2011 | Biedermann et al. |
| 2011/0093015 A1 | 4/2011 | Ramsay et al. |
| 2011/0106174 A1 | 5/2011 | Rezach |
| 2011/0106175 A1 | 5/2011 | Rezach |
| 2011/0166610 A1 | 7/2011 | Altarac et al. |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0184473 A1 | 7/2011 | Garcia-Bengochea et al. |
| 2011/0190822 A1 | 8/2011 | Spitler et al. |
| 2011/0202094 A1 | 8/2011 | Pereira et al. |
| 2011/0202095 A1 | 8/2011 | Semler et al. |
| 2011/0263945 A1 | 10/2011 | Peterson et al. |
| 2011/0313460 A1 | 12/2011 | McLean et al. |
| 2011/0313463 A1 | 12/2011 | McLean |
| 2011/0313471 A1 | 12/2011 | McLean et al. |
| 2012/0232598 A1 | 9/2012 | Hestad et al. |
| 2012/0239151 A1 | 9/2012 | Ulrich, Jr. et al. |

FOREIGN PATENT DOCUMENTS

| | | |
|---|---|---|
| DE | G9202745.8 | 4/1992 |
| DE | 4239716 | 8/1994 |
| DE | 4425392 | 11/1995 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1210914 | 6/2002 |
| EP | 1570795 | 2/2005 |
| EP | 1579816 | 9/2005 |
| EP | 1634537 | 3/2006 |
| EP | 1925263 | 5/2008 |
| EP | 2082709 | 7/2009 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| FR | 2925288 | 6/2009 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | 8912431 | 12/1989 |
| WO | 9116020 | 10/1991 |
| WO | WO92/03100 | 3/1992 |
| WO | 9321848 | 11/1993 |
| WO | 9410944 | 5/1994 |
| WO | WO94/10927 | 5/1994 |
| WO | WO94/26191 | 11/1994 |
| WO | 9428824 | 12/1994 |
| WO | 9531947 | 11/1995 |
| WO | 9606576 | 3/1996 |
| WO | 9621396 | 7/1996 |
| WO | 9628105 | 9/1996 |
| WO | 9628118 | 9/1996 |
| WO | WO96/41582 | 12/1996 |
| WO | 9714368 | 4/1997 |
| WO | 9727812 | 8/1997 |
| WO | 9801091 | 1/1998 |
| WO | 9815233 | 4/1998 |
| WO | 9825534 | 6/1998 |
| WO | 9832386 | 7/1998 |
| WO | 9834554 | 8/1998 |
| WO | 9838924 | 9/1998 |
| WO | 9905980 | 2/1999 |
| WO | 9938463 | 8/1999 |
| WO | 9947083 | 9/1999 |
| WO | 0022997 | 4/2000 |
| WO | 0027297 | 5/2000 |
| WO | 0065268 | 11/2000 |
| WO | 0066045 | 11/2000 |
| WO | WO01/10317 | 2/2001 |
| WO | 0115612 | 3/2001 |
| WO | 0128435 | 4/2001 |
| WO | WO01/28436 | 4/2001 |
| WO | WO01/45576 | 6/2001 |
| WO | 0149191 | 7/2001 |
| WO | 0167972 | 9/2001 |
| WO | 0167974 | 9/2001 |
| WO | 0234150 | 5/2002 |
| WO | WO02/054966 | 7/2002 |
| WO | WO02/102259 | 12/2002 |
| WO | 03007828 | 1/2003 |
| WO | WO03/026523 | 4/2003 |
| WO | 03047442 | 6/2003 |
| WO | WO03/068088 | 8/2003 |
| WO | 2004022108 | 3/2004 |
| WO | WO2004/041100 | 5/2004 |
| WO | WO2004/075778 | 9/2004 |
| WO | WO2004/089245 | 10/2004 |
| WO | 2004098452 | 11/2004 |
| WO | WO2004/107997 | 12/2004 |
| WO | WO2005/000136 | 1/2005 |
| WO | WO2005/000137 | 1/2005 |
| WO | 2005018466 | 3/2005 |
| WO | WO2005/020829 | 3/2005 |
| WO | 2005030068 | 4/2005 |
| WO | WO2005/065374 | 7/2005 |
| WO | WO2005/065375 | 7/2005 |
| WO | WO2005/072632 | 8/2005 |
| WO | 2005087121 | 9/2005 |
| WO | WO2005/082262 | 9/2005 |
| WO | WO2005/099400 | 10/2005 |
| WO | 2005102195 | 11/2005 |
| WO | WO2005/104969 | 11/2005 |
| WO | WO2006/005198 | 1/2006 |

(56) References Cited

FOREIGN PATENT DOCUMENTS

| | | |
|---|---|---|
| WO | WO2006/012088 | 2/2006 |
| WO | WO2006/017616 | 2/2006 |
| WO | WO2006/020530 | 2/2006 |
| WO | WO2006/028537 | 3/2006 |
| WO | 2006042188 | 4/2006 |
| WO | WO2006/045094 | 4/2006 |
| WO | 2006047711 | 5/2006 |
| WO | 2006066685 | 6/2006 |
| WO | 2006079531 | 8/2006 |
| WO | WO2006/086537 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006119447 | 11/2006 |
| WO | WO2006/116662 | 11/2006 |
| WO | WO2006/119241 | 11/2006 |
| WO | WO2007/002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007044705 | 4/2007 |
| WO | 2007053566 | 5/2007 |
| WO | 2007060534 | 5/2007 |
| WO | 2007075454 | 7/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007121271 | 10/2007 |
| WO | WO2007/118045 | 10/2007 |
| WO | 2007123920 | 11/2007 |
| WO | 2007124249 | 11/2007 |
| WO | 2007127595 | 11/2007 |
| WO | 2007127604 | 11/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008036975 | 3/2008 |
| WO | 2008039777 | 4/2008 |
| WO | 2008042948 | 4/2008 |
| WO | 2008048923 | 4/2008 |
| WO | WO2008/045210 | 4/2008 |
| WO | 2008070716 | 6/2008 |
| WO | WO2008/069420 | 6/2008 |
| WO | 2008078163 | 7/2008 |
| WO | 2008082737 | 7/2008 |
| WO | WO2008/088731 | 7/2008 |
| WO | WO2008/088990 | 7/2008 |
| WO | WO2008/089075 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008134703 | 11/2008 |
| WO | WO2008/140756 | 11/2008 |
| WO | 2008157589 | 12/2008 |
| WO | 2009006225 | 1/2009 |
| WO | 2009011845 | 1/2009 |
| WO | WO2009/015100 | 1/2009 |
| WO | WO2005/013839 | 2/2009 |
| WO | 2009029928 | 3/2009 |
| WO | WO2009/036541 | 3/2009 |
| WO | 2009055407 | 4/2009 |
| WO | 2009152302 | 12/2009 |
| WO | 2009155360 | 12/2009 |
| WO | WO2010/018316 | 2/2010 |
| WO | WO2010/018317 | 2/2010 |
| WO | WO2010/019704 | 2/2010 |
| WO | WO2010/019857 | 2/2010 |
| WO | 2010030916 | 3/2010 |
| WO | 2010045383 | 4/2010 |
| WO | 2010065648 | 6/2010 |

OTHER PUBLICATIONS

Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
Brochure of Tyco/Healthcare/Surgical Dynamics on Spiral Radius 90D, Publication Date: Sep. 2001, pp. 1-8.
Brochure of Zimmer Spine, Inc., Dynesys® LIS Less Invasive Surgery, The Dynamic Stabilization System, Publication Date: 2005.
Claris Instrumentation Brochure, G Med, pub. 1997.
EBI Omega 21 Brochure, EBI Spine Systems, pub. 1999.
SDRS Surgical Dynamics Rod System Brochure, Surgical Dynamics, pub. 1998-99.
Spine, Lipcott, Williams & Wilkins, Inc. vol. 24, No. 15, p. 1495.
The Rod Plate System Brochure, Stryker HowmedicaOsteonics, pub. Oct. 1999.
Versalok Low Back Fixation System Brochure, Wright Medical Technology, Inc., pub. 1997.
VLS System Variable Locking Screw Brochure, Interpore Cross International, 1999.
Brochure of DePuySpine on Surgical Technique, Published 2004, pp. 1-36.

* cited by examiner

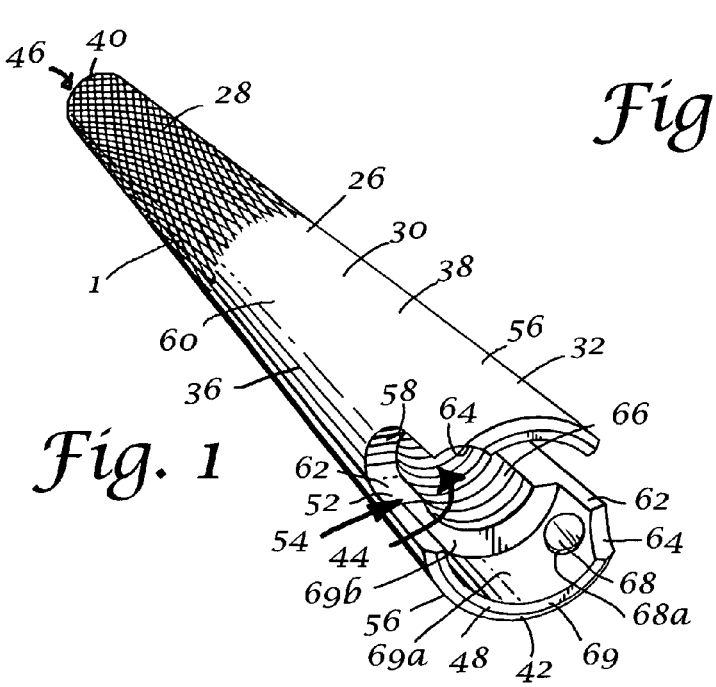
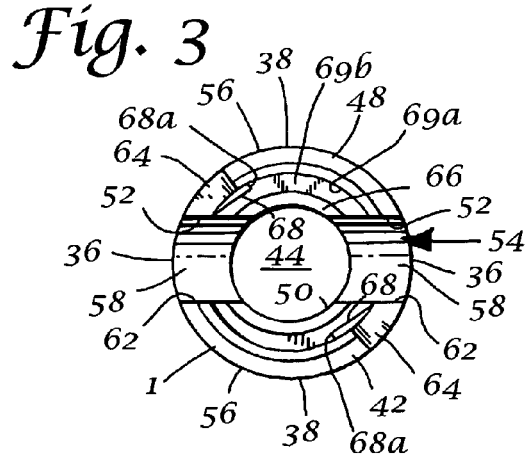
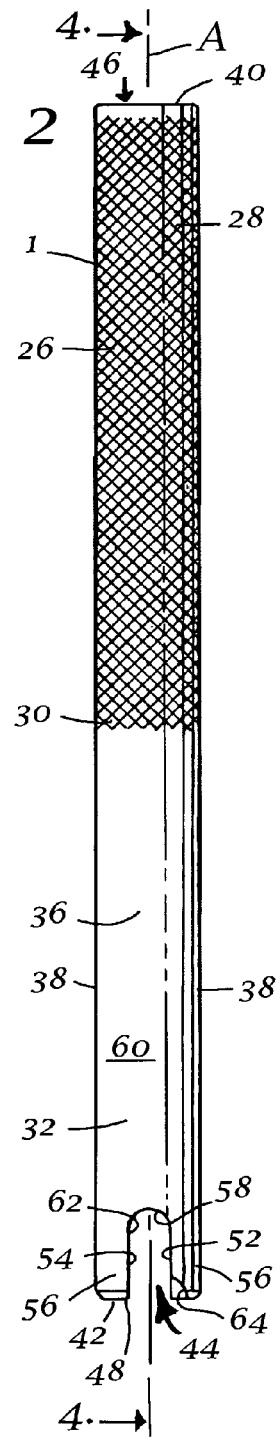

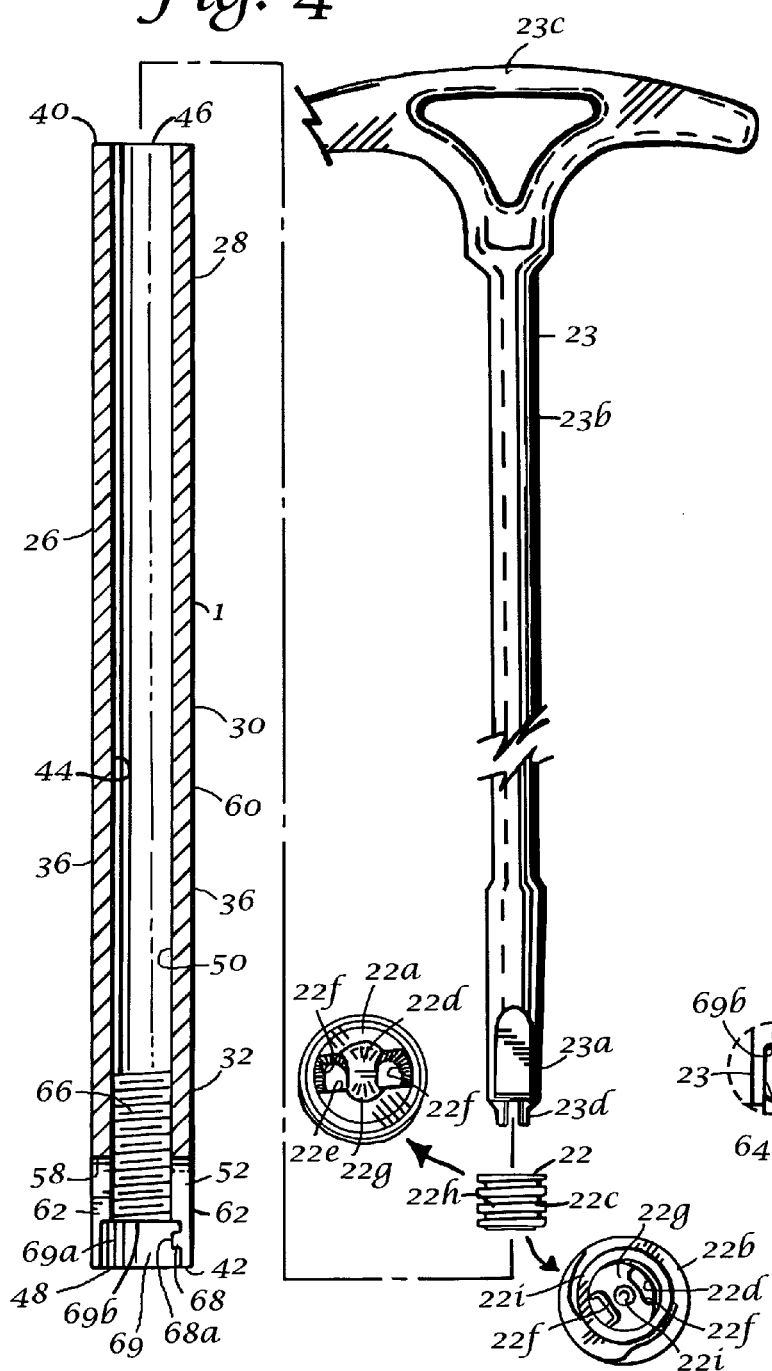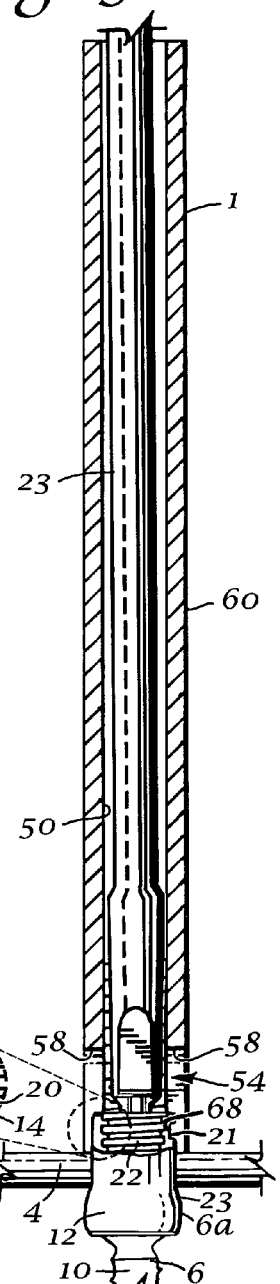

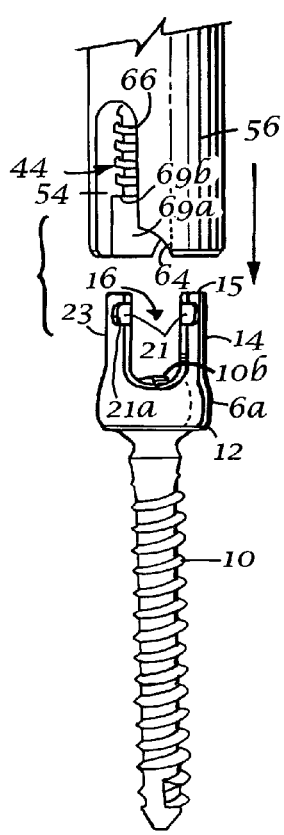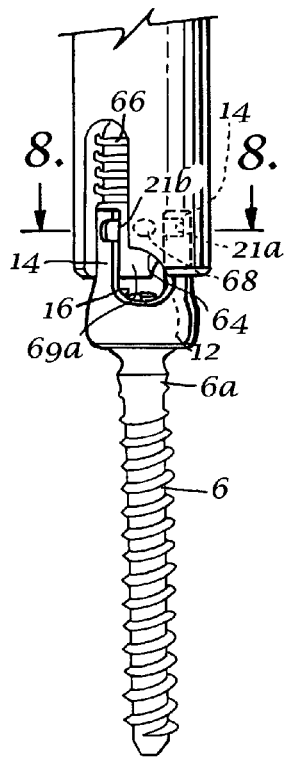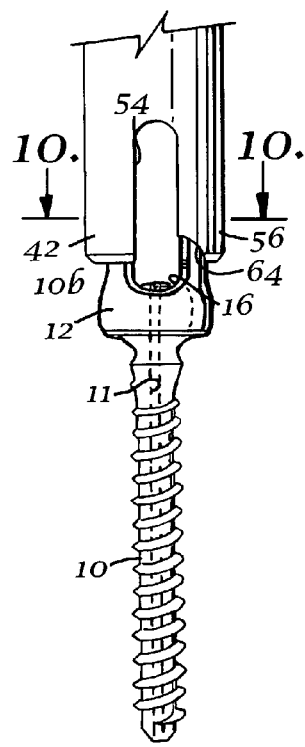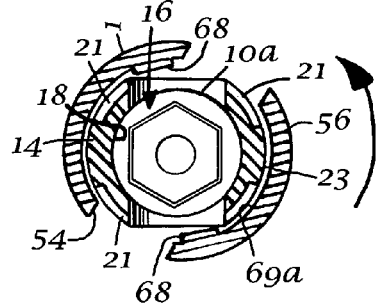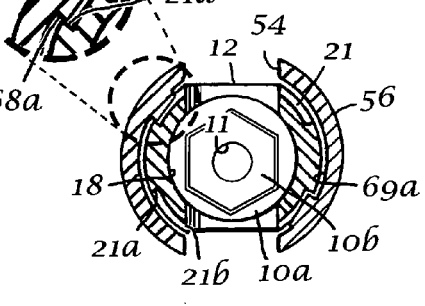

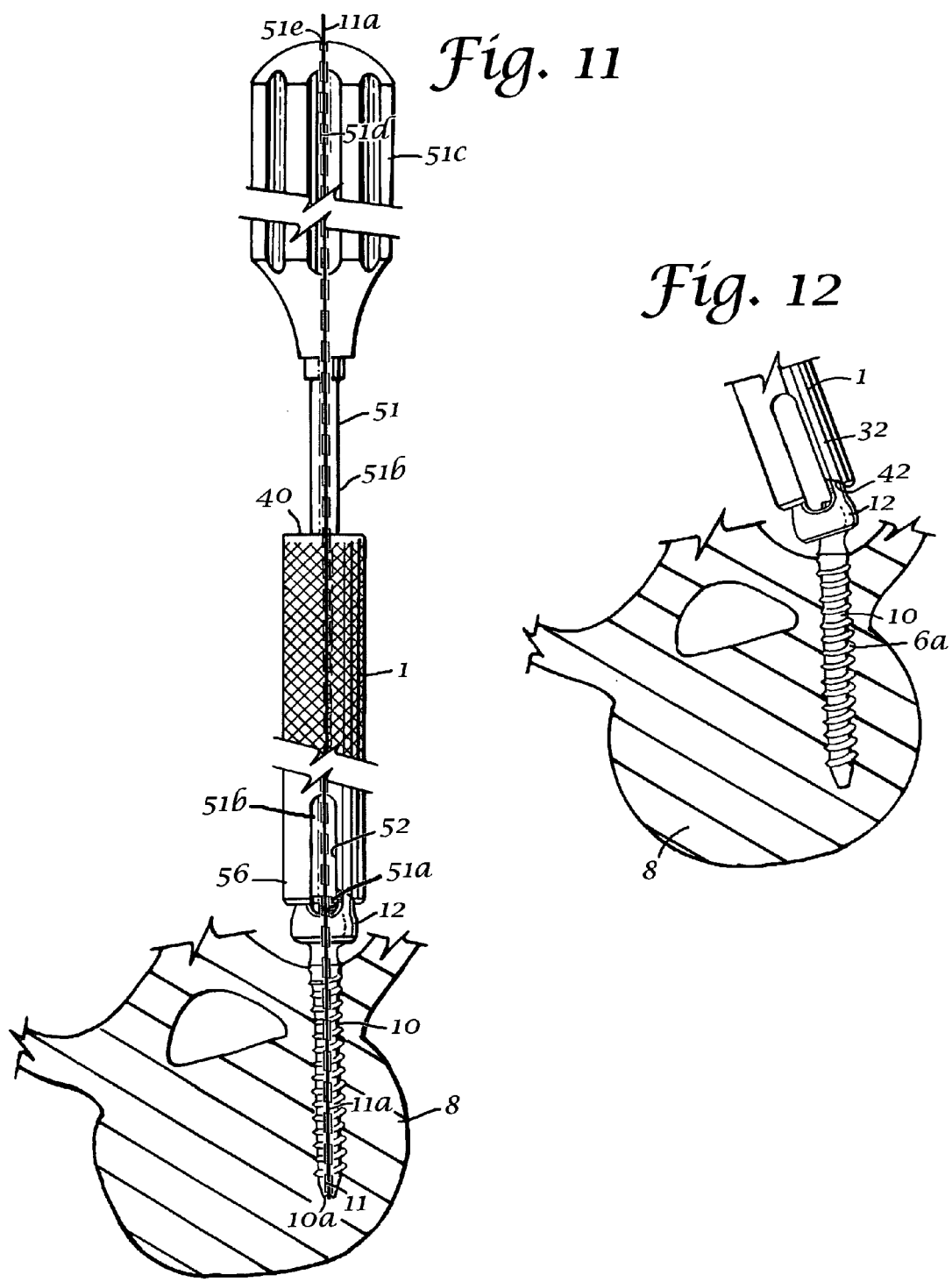

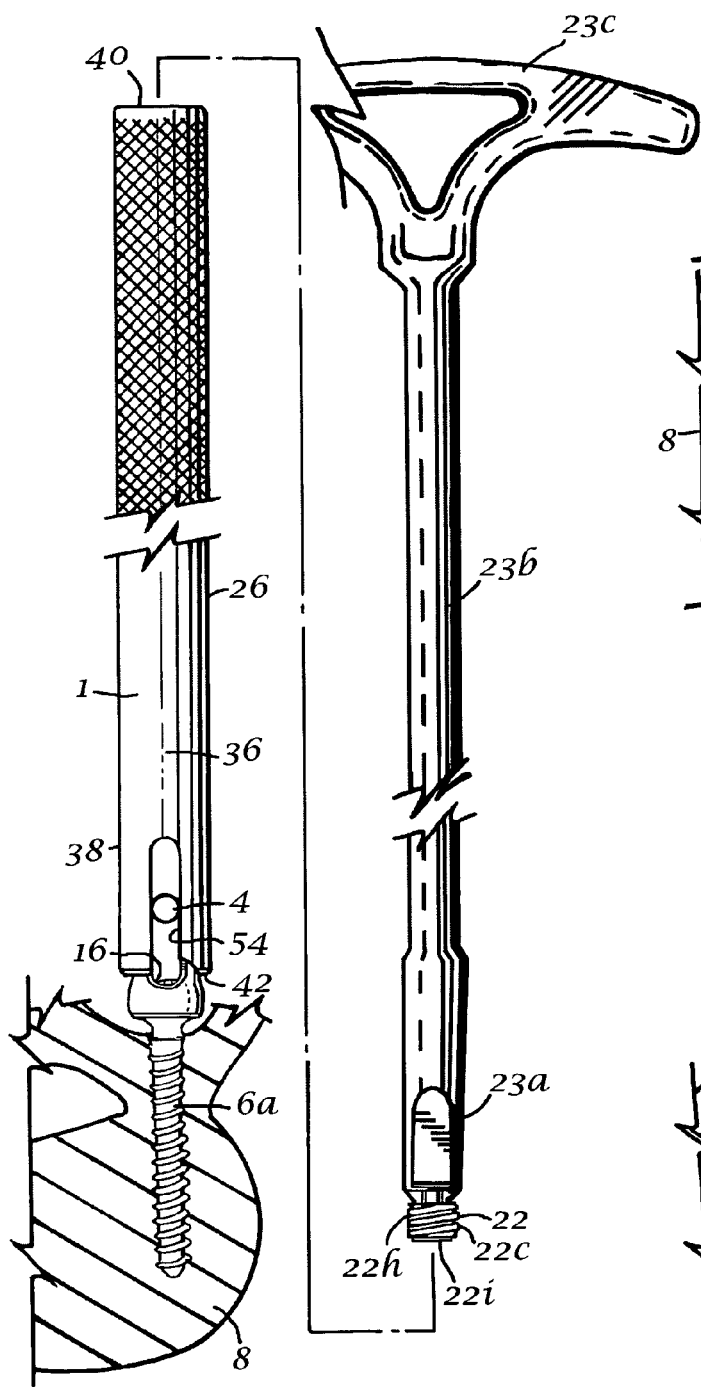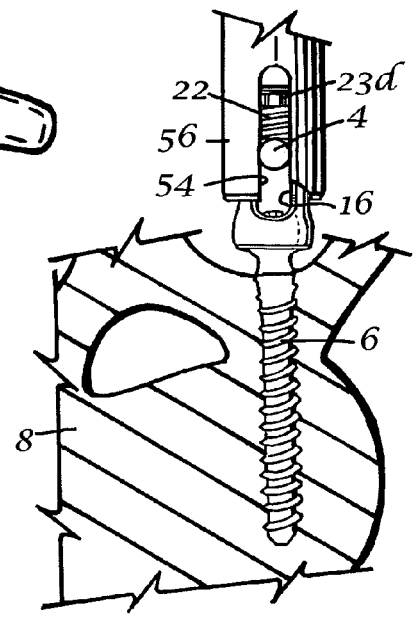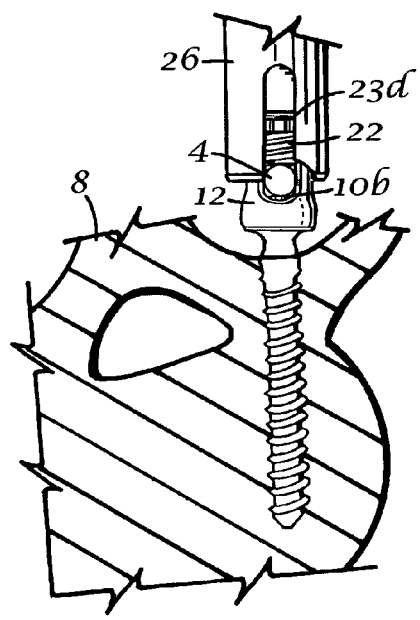

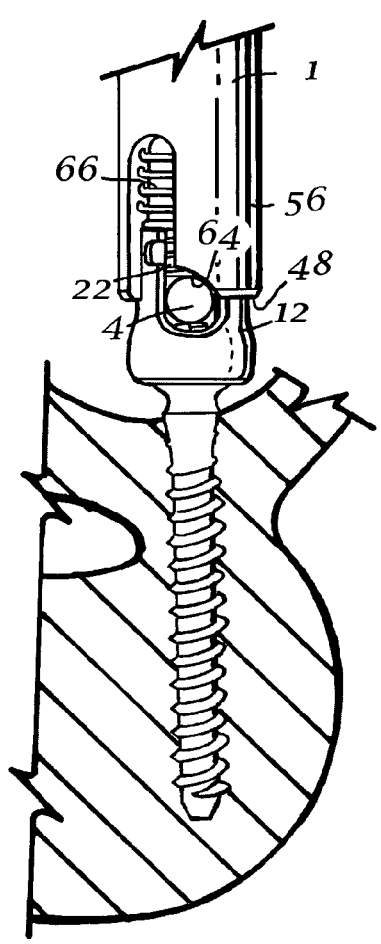
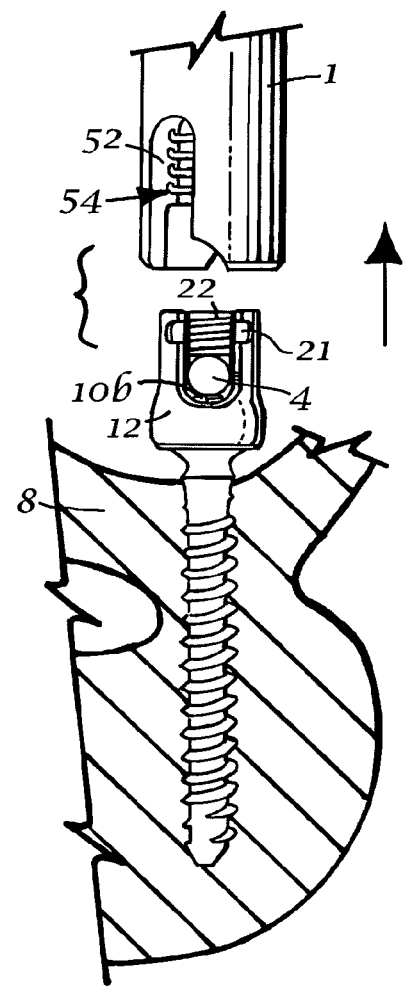

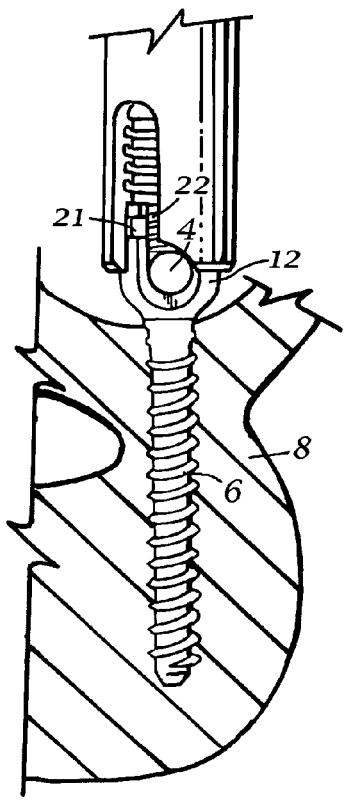
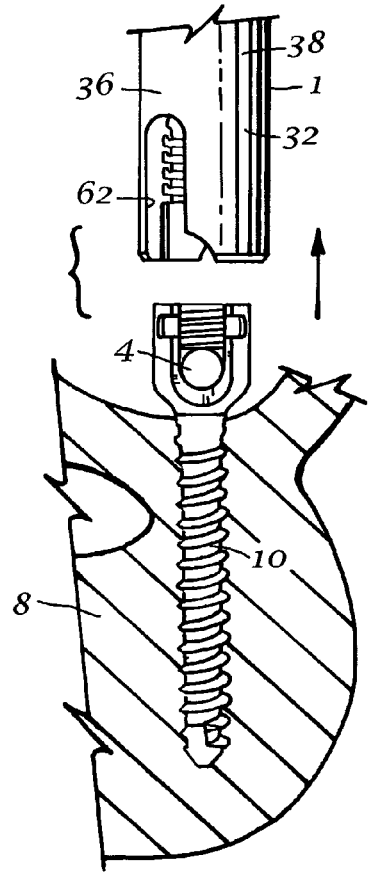
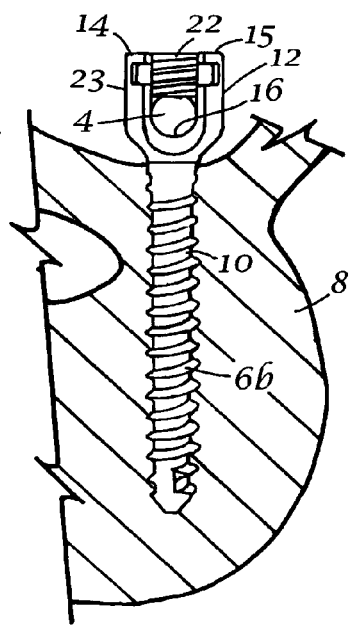

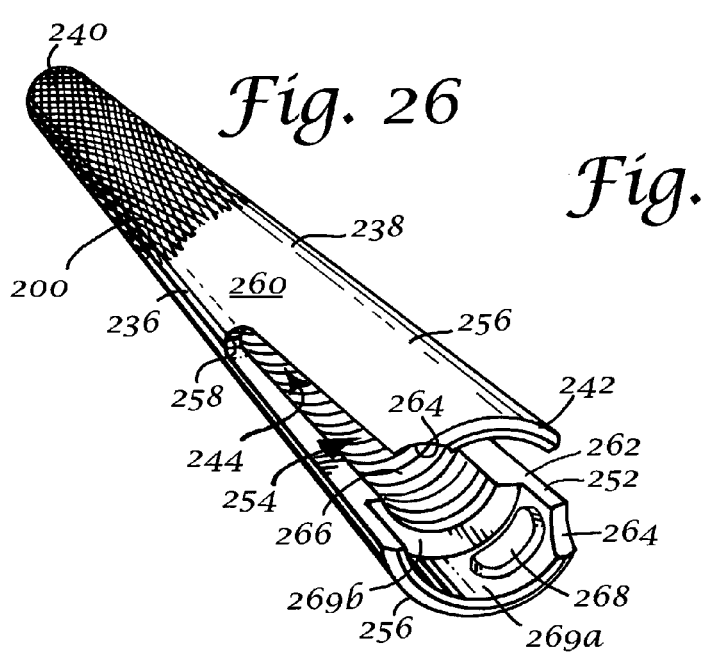
Fig. 26
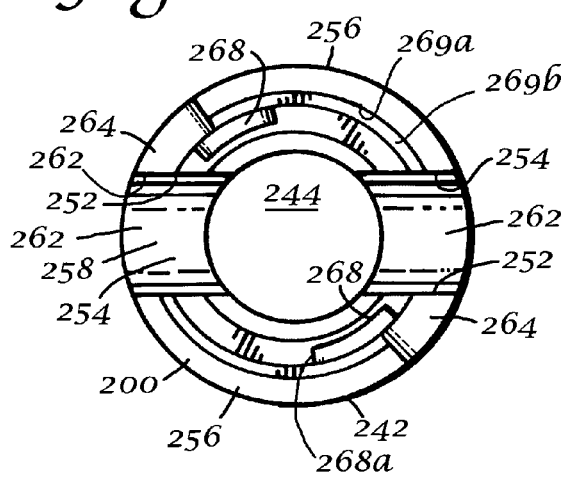
Fig. 28
Fig. 27
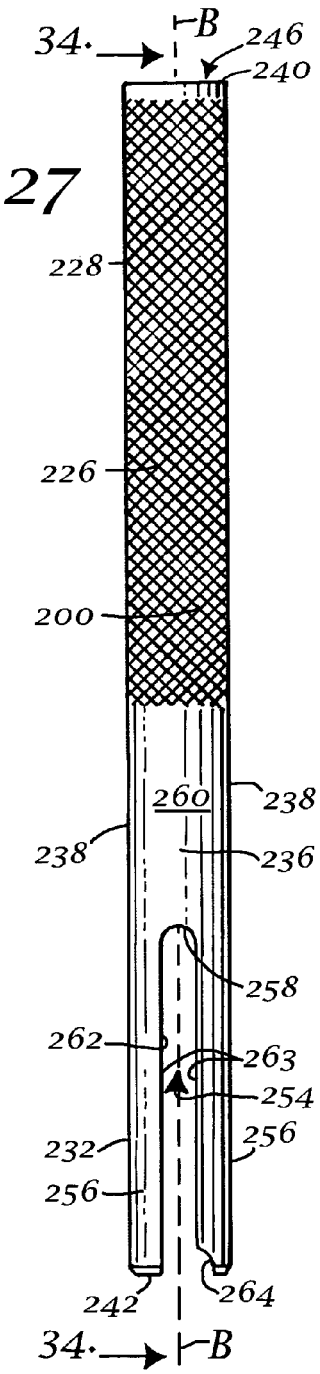

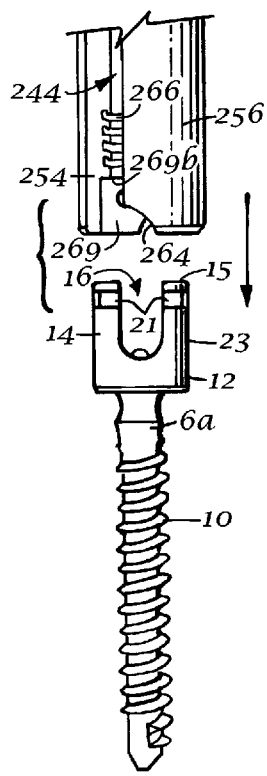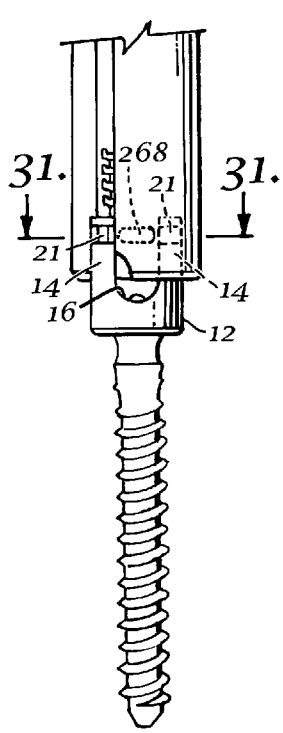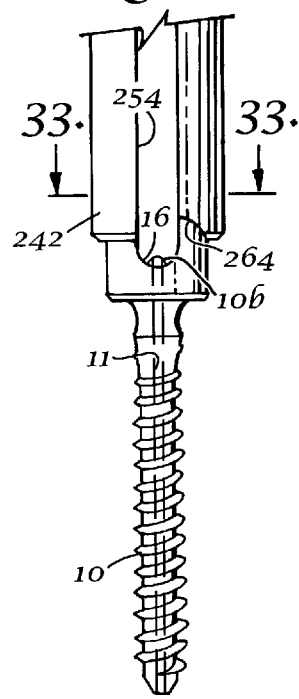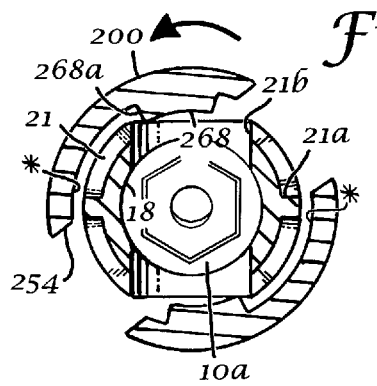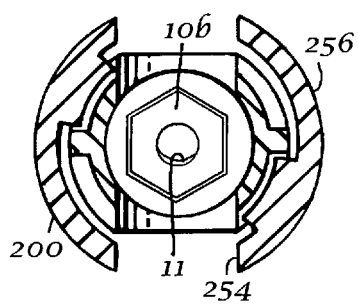

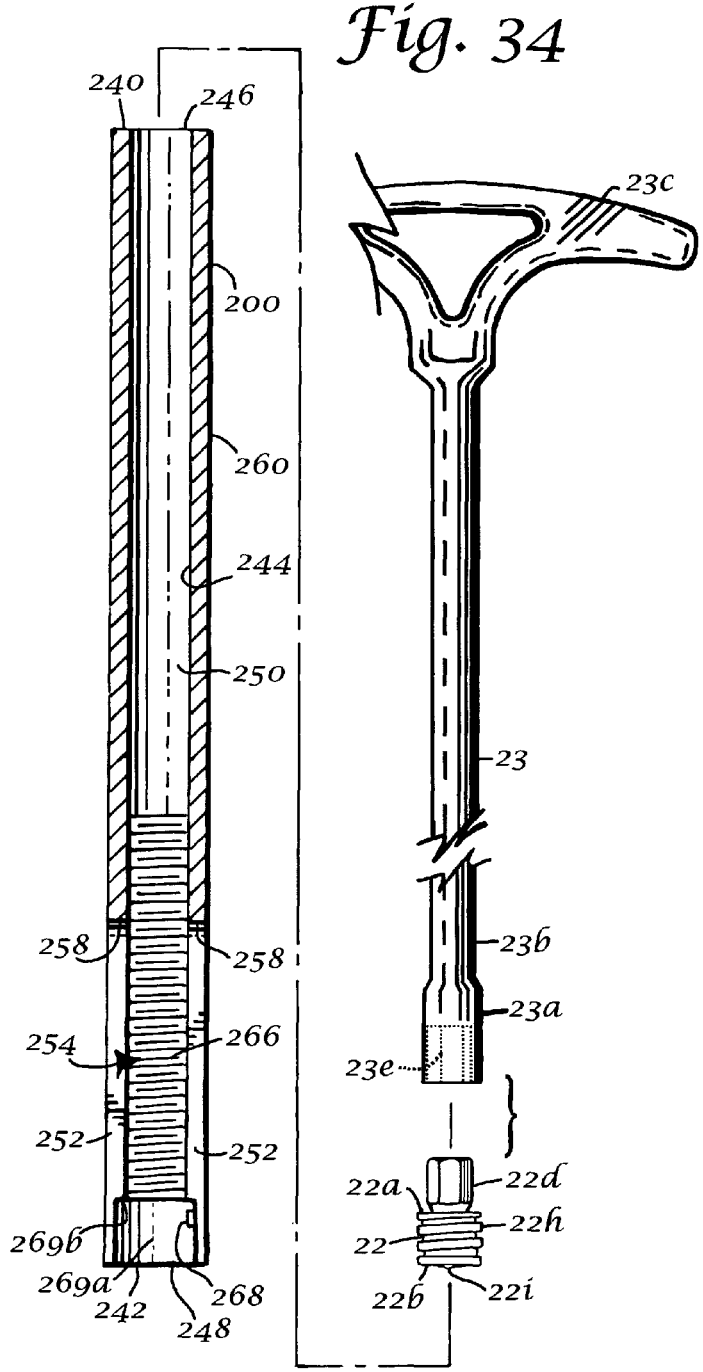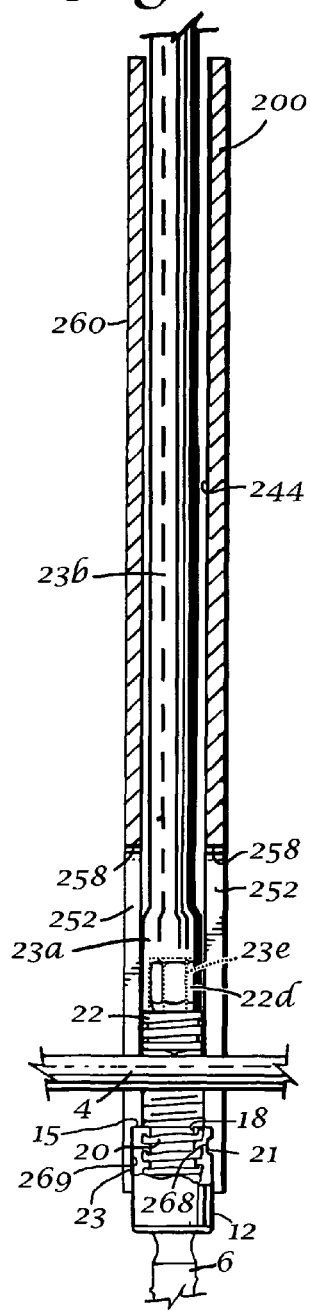

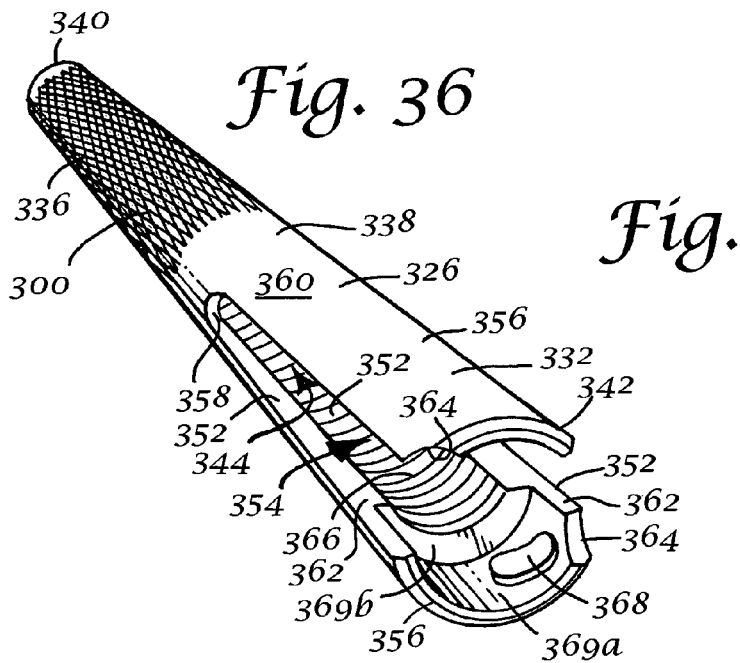
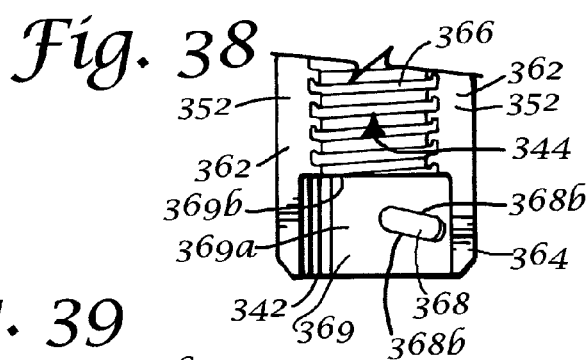
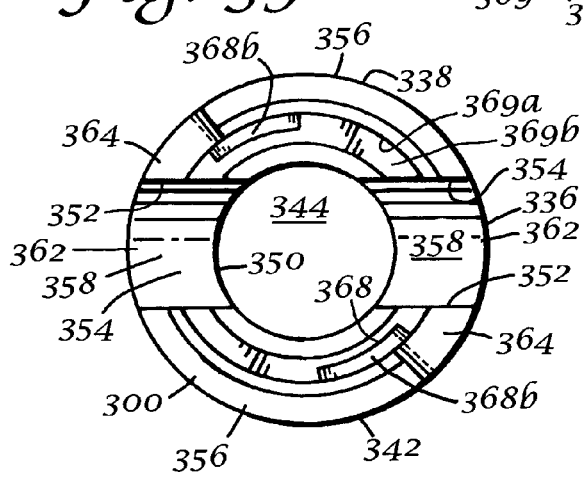
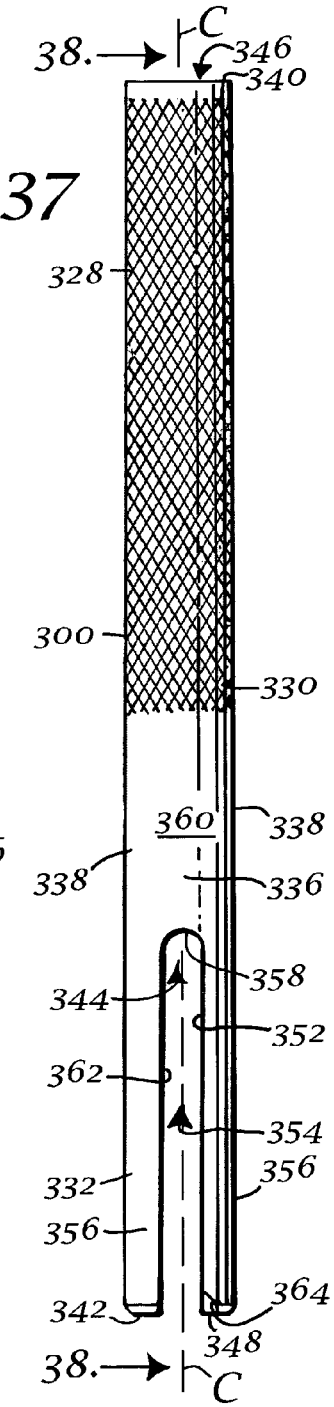

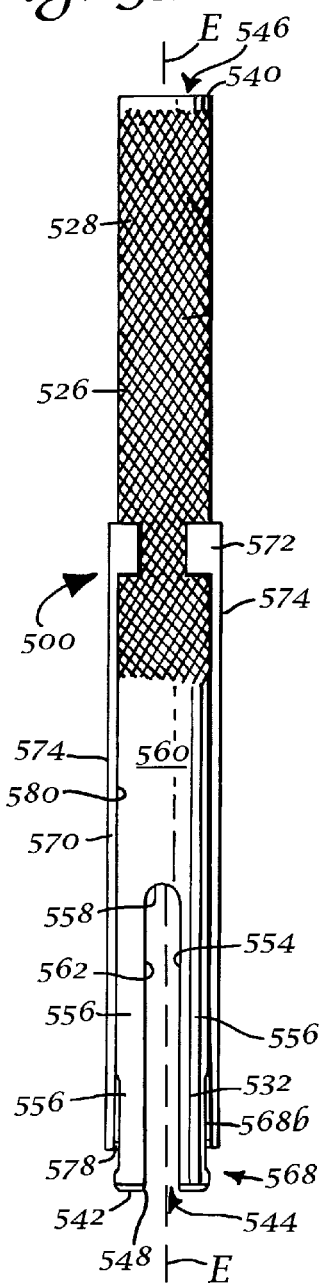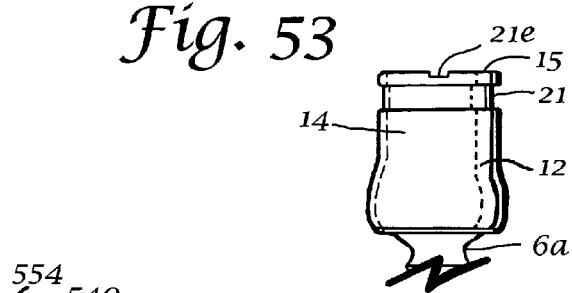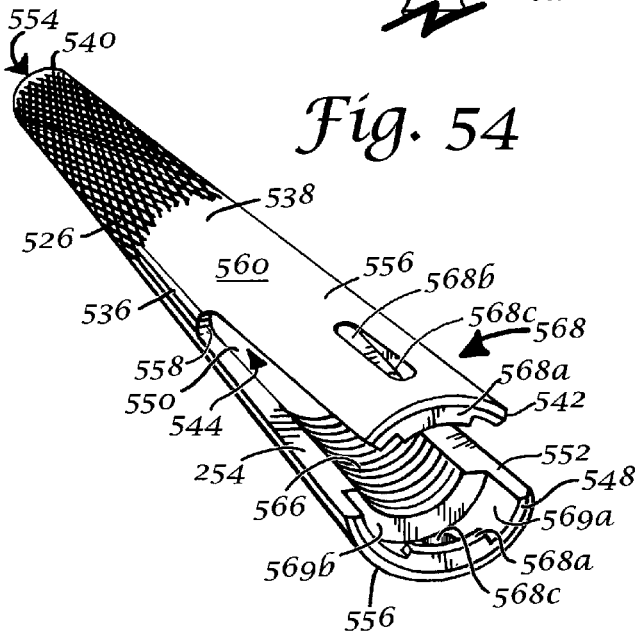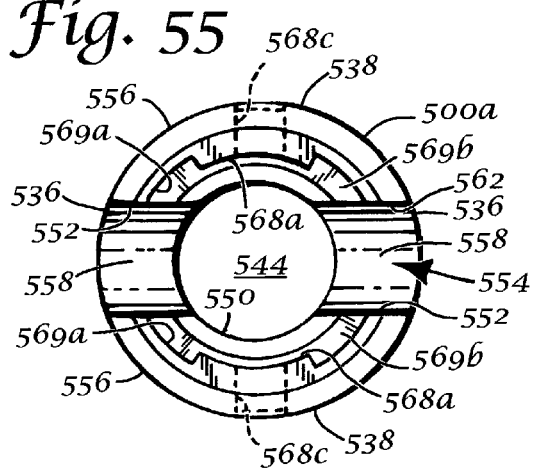

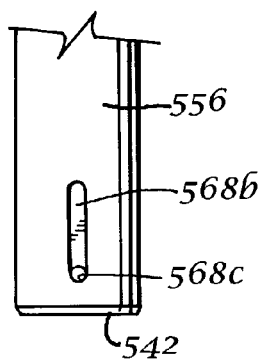
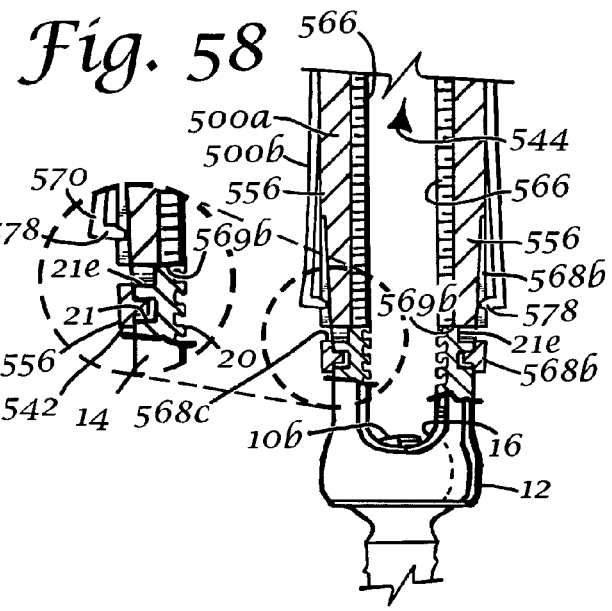
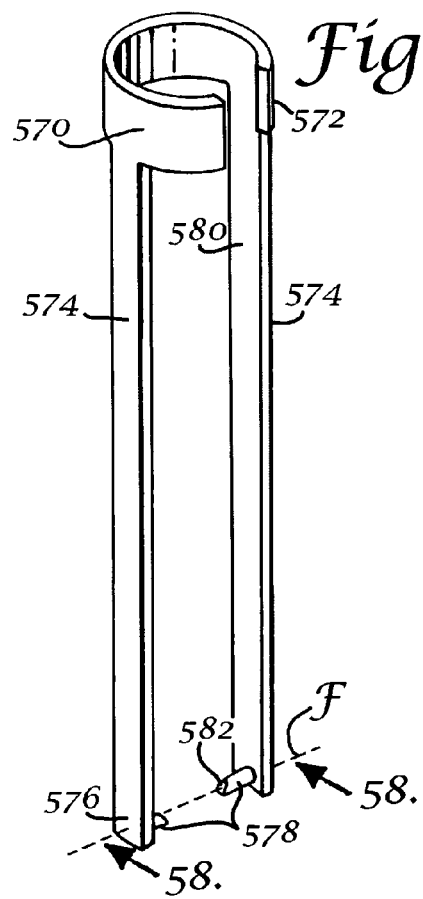
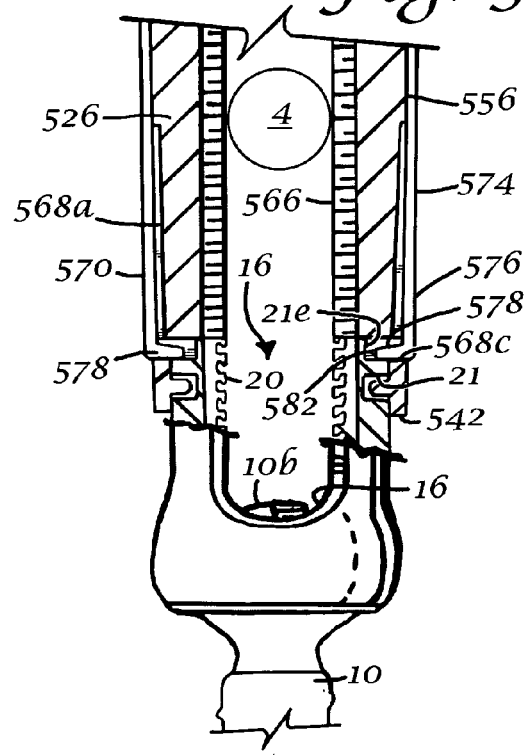

US 9,050,139 B2

ORTHOPEDIC IMPLANT ROD REDUCTION TOOL SET AND METHOD

CROSS-REFERENCE TO RELATED APPLICATION

This application is a continuation-in-part of U.S. patent application Ser. No. 13/374,932, filed Jan. 24, 2012, now U.S. Pat. No. 8,377,067, which is continuation of U.S. patent application Ser. No. 12/584,413, filed Sep. 4, 2009 and which issued as U.S. Pat. No. 8,100,915 on Jan. 24, 2012, which is as a continuation of U.S. patent application Ser. No. 12/220,185, filed Jul. 22, 2008, which is a Division of U.S. patent application Ser. No. 11/502,926, filed Aug. 11, 2006 and now abandoned, which is a Division of U.S. patent application Ser. No. 10/789,149, filed Feb. 27, 2004 and which issued as U.S. Pat. No. 7,160,300 on Jan. 9, 2007, all of which are incorporated herein by reference. This application is also a continuation-in-part of U.S. patent application Ser. No. 11/272,508, filed Nov. 10, 2005, which claims Priority from U.S. Provisional Application No. 60/630,536, filed Nov. 23, 2004, and is a Continuation-in-part of U.S. patent application Ser. No. 10/996,289, filed Nov. 23, 2004 and which issued as U.S. Pat. No. 8,152,810 on Apr. 10, 2012, which is a Continuation-in-part of U.S. patent application Ser. No. 10/789,149, filed Feb. 27, 2004 and which issued as U.S. Pat. No. 7,160,300 on Jan. 9, 2007, all of which are incorporated herein by reference.

BACKGROUND OF THE INVENTION

The present invention relates to apparatuses and methods for use in performing spinal surgery and, in particular, to tools and methods of using such tools, especially for percutaneously implanting a rod for spinal support and alignment using minimally invasive techniques.

For many years, spinal osteosynthesis apparatuses have been utilized to correct spinal deformities, injuries or disease. In such procedures, elongate rods are surgically attached to vertebrae of the spine to provide support and/or to reposition certain vertebrae. Such rods are secured to vertebrae utilizing bone screws and other implants.

Surgical techniques and bone screws have improved; however, in order to reduce the impact of such surgery on the patient, it has been desirable for such implants to be inserted percutaneously or with surgical techniques that are minimally invasive to the body of the patient. This presents a problem with implantation of rods that are elongate and have historically required a long incision and open wound in order to provide for the length of the rod and the space required for the surgeon's hands to manipulate the rod, implants and insertion tools used with the rod. Consequently, it has been desirable to develop apparatuses and techniques that allow for the insertion of bone screws, the insertion and reduction of a rod and the securing of the rod to the bone screws with significantly reduced invasion into the body of the patient and with minimal incision size in the skin over the operational site.

SUMMARY OF THE INVENTION

In a first embodiment an elongate guide tool in combination with a spinal bone screw implant are provided. The guide tool is reversibly attachable to the bone screw and is useful for guiding a rod into a receiver of the bone screw during a minimally invasive percutaneous surgical procedure. The guide tool includes a body with a longitudinally extending through-bore that extends from a top opening to a bottom opening. The through-bore is sized and shaped for receiving a closure top therethrough. The guide tool also includes a laterally extending pass-through slot that extends upwardly from the body bottom opening and is joined with the through-bore. The guide tool body includes upper, middle and lower portions and the pass-through slot extends from the lower portion toward the middle portion.

The pass-through slot defines a pair of spaced opposed legs and is sized and shaped so as to receive a rod therethrough. The pass-through slot is alignable with a U-shaped channel of the bone screw upon rotation attachment of the guide tool onto the bone screw. The guide tool also includes a first attachment structure that is sized and shaped to cooperatively engage a second attachment structure of the bone screw when the guide tool is secured to the bone screw. The first and second attachment structures are complementary in size and shape. Additionally, when the pass-through slot and the U-shaped channel are aligned, the rod is transferable from the guide tool to the bone screw.

In a further embodiment, the guide tool also includes a cutout or relief portion that is sized, shaped and positioned so as to straddle a rod installed in the bone screw U-shaped channel when the guide tool is rotated such that the pass-through slot and the U-shaped channel are not aligned.

In another further embodiment, each of the legs includes an inner surface that includes the first attachment structure. The guide tool first attachment structure reversibly engages the bone screw second attachment structure upon rotation of the guide tool relative to a head of the bone screw. The first and second attachment structures cooperate so as to substantially align the guide tool pass-through slot and the bone screw U-shaped channel such that the rod is transferable therebetween. Each of the leg inner surfaces may also include a portion of a guide and advancement structure thereon.

In yet another further embodiment, the first attachment structure includes an off-set detent sized and shaped so as to be cooperatively rotatably received by the bone screw second attachment structure. Accordingly, the bone screw second attachment structure is an off-axis partially circumferential slot sized and shaped to reversibly engage the off-set detent.

In another further embodiment, the first attachment structure includes an off-set cam sized and shaped so as to be cooperatively rotatably received by the bone screw second attachment structure. Accordingly, the bone screw second attachment structure is a camming groove or slot sized and shaped to reversibly engage the off-set cam.

In still another further embodiment, the first attachment structure includes an inwardly extending shelf near the guide tool bottom opening, the shelf being sized and shaped so as to be cooperatively rotatably engage the bone screw second attachment structure. Accordingly, the bone screw second attachment structure is a partially circumferential, slot or notch sized and shaped to rotatably receive the shelf therein.

In some embodiments, each of the guide tool legs includes a recessed radially extending pin-receiving bore joining an inner surface of the leg with an outer surface of the body. The pin-receiving bores are opposed to one another. The guide tool also includes an engagement member attached to the body and which has a pair of longitudinally extending inwardly biased tangs. Each of the tangs includes an inwardly extending lower engagement pin sized, shaped and located so as to reversibly extend through a respective pin-receiving bore and reversibly engage a bone screw second attachment structure. The pin-receiving bores are substantially coaxial. In some further embodiments, each of the legs further includes a bottom ridge sized and shaped for reversible engagement by a cooperatively shaped bone screw second attachment structure.

The drawings constitute a part of this specification and include exemplary embodiments of the present invention and illustrate various objects and features thereof.

BRIEF DESCRIPTION OF THE DRAWINGS

FIG. 1 is perspective view of a guide tool for percutaneously implanting a rod in a patient, in a first embodiment.

FIG. 2 is a reduced side view of the guide tool of FIG. 1.

FIG. 3 is an enlarged bottom view of the guide tool of FIG. 1.

FIG. 4 is a cross section of the tool of FIG. 2 taken along line 4-4 of FIG. 2, including a closure top adapted for use with the guide tool and a closure installation tool or driver for installing the closure top into a bone screw attached to the guide tool, and including enlarged top and bottom views of the closure.

FIG. 5 is an enlarged view of a portion of the tool of FIG. 4 including a polyaxial bone screw adapted for use with the tool of FIG. 1, a rod, the closure of FIG. 4 and the closure driver of FIG. 4, showing attachment of the guide tool to the bone screw and installation of the closure top into the bone screw head using the closure driving tool, so as to secure a rod in the bone screw head.

FIG. 6 an enlarged side view of the guide tool of FIG. 1 with portions broken away showing an initial step in reversibly attaching the guide tool to the polyaxial bone screw of FIG. 5.

FIG. 7 is a side view of the guide tool of FIG. 6 showing an intermediate step in attaching the guide tool of FIG. 1 to the polyaxial bone screw of FIG. 6, wherein the through-slot of the guide tool is not yet aligned with the U-shaped channel of the bone screw.

FIG. 8 is an enlarged cross-sectional view of the guide tool and bone screw of FIG. 7 taken along the line 8-8 of FIG. 7 and illustrating the an initial step in aligning and engaging the guide tool bone screw attachment structure with the complementary bone screw tool engagement structure.

FIG. 9 is a side view of the guide tool of FIG. 7 showing the guide tool of FIG. 1 reversibly attached to a polyaxial bone screw of FIG. 6, wherein the guide tool has been rotated about 90-degrees clockwise relative to the bone screw head and the guide tool through-slot is substantially aligned with the bone screw U-shaped channel.

FIG. 10 is an enlarged cross-sectional view of the guide tool and bone screw of FIG. 9 taken along the lines 10-10 of FIG. 9 and illustrating reversible engagement of the guide tool bone screw attachment structure with the bone screw tool engagement structure.

FIG. 11 is a side view of the tool of FIG. 2 with an attached polyaxial bone screw illustrating driving the bone screw into a vertebra using a bone screw driver adapted for use with the bone screw and the guide tool and also showing, in phantom, a guide wire extending upwardly through a cannula in the bone screw and through a cannula in the bone screw driver.

FIG. 12 is a side view of the guide tool of FIG. 11, with portions broken away and after the bone screw driver has been removed, illustrating use of the guide tool to adjust the position of the bone screw head relative to the bone screw shank.

FIG. 13 is a reduced side view of the guide tool of FIG. 1 showing the guide tool attached to the polyaxial bone screw of FIG. 6, including a rod, a closure top adapted for use with the guide tool and the bone screw and also a closure installation tool adapted for use with the guide tool and the bone screw.

FIG. 14 is a side view of the guide tool of FIG. 13, with portions broken away, illustrating a step of guiding the rod into the bone screw and of installing the closure top.

FIG. 15 is a side view of the guide tool of FIG. 14 in a further step of installing the rod and the closure top into the bone screw U-shaped channel using the closure installation tool.

FIG. 16 is a side view of the guide tool of FIG. 15 illustrating an initial step in disengaging the guide tool from the bone screw after installation of the rod and the closure top in the bone screw.

FIG. 17 is a side view of the guide tool of FIG. 16, illustrating a further step in the removal of the guide tool removed from the bone screw.

FIG. 23 is a side view of the guide tool and monoaxial bone screw of FIG. 21 illustrating a step in detaching the guide tool from the monoaxial bone screw after installation of a rod and a closure top into the monoaxial bone screw.

FIG. 24 is a side view of the guide tool and monoaxial bone screw of FIG. 23 illustrating a further step in detaching the guide tool from the monoaxial bone screw.

FIG. 25 is a side view of the monoaxial bone screw of FIG. 24, with the rod and closure top installed, and after the guide tool has been detached.

FIG. 26 is perspective view of a guide tool for percutaneously implanting a rod in a patient, in a second embodiment.

FIG. 27 is a reduced side view of the guide tool of FIG. 26.

FIG. 28 is an enlarged bottom view of the guide tool of FIG. 26.

FIG. 29 is an enlarged side view of the guide tool of FIG. 26, with portions broken away, illustrating an initial step in attaching the guide tool of FIG. 26 to a polyaxial bone screw adapted for use with the guide tool of FIG. 26.

FIG. 30 is a side view of the guide tool and polyaxial bone screw of FIG. 29 illustrating an intermediate step in attaching the guide tool to the polyaxial bone screw, wherein the guide tool through-slot is not yet aligned with the bone screw U-shaped channel.

FIG. 31 is an enlarged cross-sectional view of the assembly of FIG. 30 taken along the line 31-31 of FIG. 30 illustrating the an initial step in aligning and engaging the guide tool bone screw attachment structure with the complementary bone screw tool engagement structure.

FIG. 32 is a side view of the assembly of FIG. 30 illustrating the guide tool attached to or mounted on the polyaxial bone screw, wherein the guide tool through-slot is substantially aligned with the bone screw U-shaped channel.

FIG. 33 is an enlarged cross-sectional view of the assembly of FIG. 32 taken along the line 33-33 of FIG. 32 illustrating the guide tool bone screw attachment structure reversibly engaged with the bone screw tool engagement structure.

FIG. 34 is a cross-section of the guide tool of FIG. 26 taken along the line 34-34 of FIG. 27, and illustrating a closure top, with a break-off head, adapted for use with the guide tool and a closure driver adapted for use with the closure top, wherein certain portions of the closure driver are shown in phantom to show greater detail thereof.

FIG. 35 is a view of the components of FIG. 34, with portions broken away, illustrating a step of installing a rod into the polyaxial bone screw of FIG. 29 in conjunction with installing the closure top of FIG. 34 using the closure driving tool of FIG. 34.

FIG. 36 is perspective view of a guide tool for percutaneously implanting a rod in a patient, in a third embodiment.

FIG. 37 is a reduced side view of the guide tool of FIG. 36.

FIG. 38 is an enlarged cross-sectional view of the guide tool of FIG. 36 taken along line 38-38 of FIG. 37, with portions broken away.

FIG. 39 is an enlarged bottom view of the guide tool of FIG. 36.

FIG. 52 is side view of a guide tool for percutaneously implanting a rod in a patient, in a fifth embodiment.

FIG. 53 is a side view of a polyaxial bone screw adapted for use with the guide tool of FIG. 52, with portions broken away.

FIG. 54 is an enlarged perspective view of a first portion of the guide tool of FIG. 52.

FIG. 55 is an enlarged bottom view of the guide tool first portion of FIG. 54.

FIG. 56 is a side view of the guide tool first portion of FIG. 54, with portions broken away.

FIG. 57 is an enlarged perspective view of a second portion of the guide tool of FIG. 52.

FIG. 58 is a partial cross-sectional view of the guide tool of FIG. 52 taken along line 58-58 of FIG. 57, and illustrating an initial step in attaching the guide tool to the polyaxial bone screw of FIG. 53.

FIG. 59 is an enlarge view of the assembly of FIG. 58 showing the guide tool reversibly attached to the polyaxial bone screw.

DETAILED DESCRIPTION OF THE INVENTION

Figure 18:
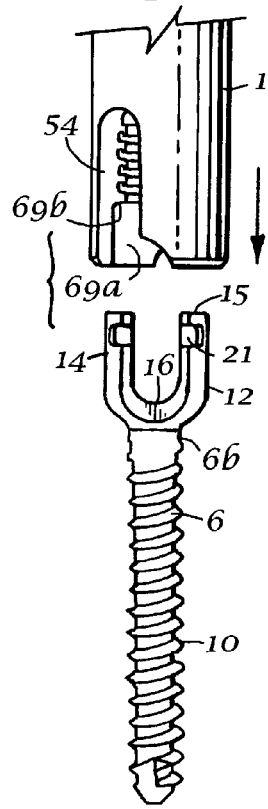
FIG. 18 is an enlarged side view of the guide tool of FIG. 1, with portions broken away, illustrating an initial step in reversibly attaching the guide tool of FIG. 1 to a monoaxial bone screw adapted for use with the guide tool.
Figure 19:
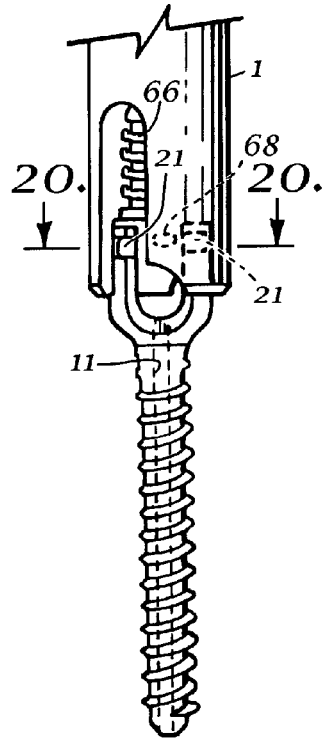
FIG. 19 is a side view of the guide tool of FIG. 18 illustrating an intermediate step in attaching the guide tool to the monoaxial bone screw, wherein the guide tool through-slot is not yet aligned with the bone screw U-shaped channel.
Figure 21:
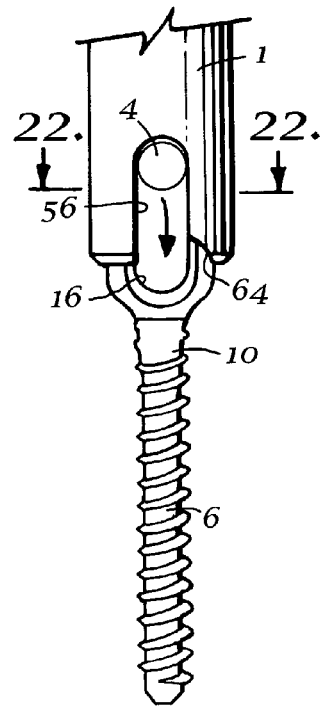
FIG. 21 is a side view of the guide tool of FIG. 19 showing the guide tool reversibly attached to the monoaxial bone screw of FIG. 18, wherein the guide tool through-slot is substantially aligned with the bone screw U-shaped channel.
Figure 20:
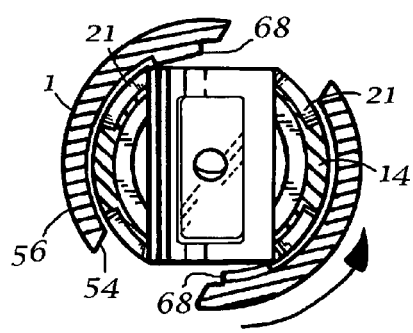
FIG. 20 is an enlarged cross-section of FIG. 19 taken along the line 20-20 of FIG. 19 and illustrating the an initial step in aligning and engaging the guide tool bone screw attachment structure with the complementary bone screw tool engagement structure.
Figure 21A:
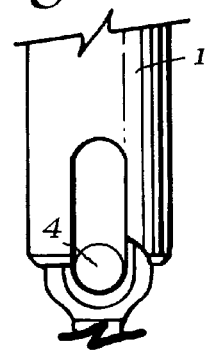
FIG. 21*a* is a side view of the assembly of FIG. 21, with portions broken away, showing the rod reduced into the bone screw U-shaped channel.
Figure 22:
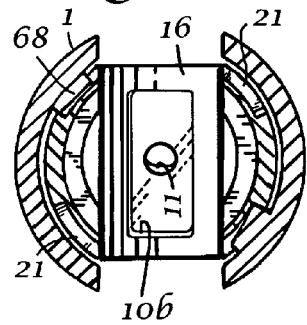
FIG. 22 is an enlarged cross-section of FIG. 21 taken along the line 22-22 of FIG. 21 showing the guide tool bone screw attachment structure reversibly engaged with the bone screw tool engagement structure.
Figure 40:
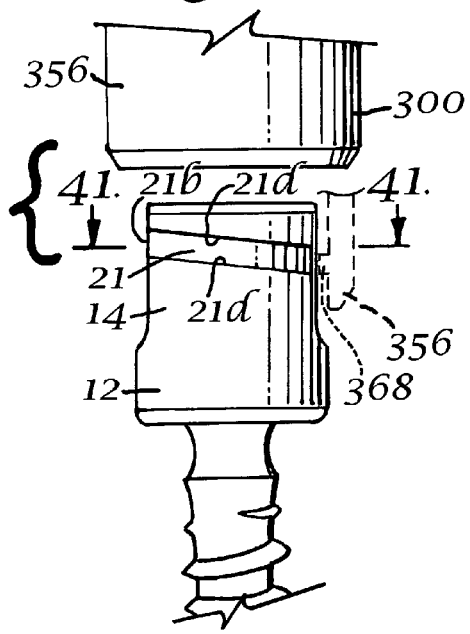
FIG. 40 is an enlarged side view of the guide tool of FIG. 36, with portions broken away to illustrate an initial step in attaching the guide tool of FIG. 36 to a polyaxial bone screw adapted for use with the guide tool, and also showing a portion of the guide tool in phantom to illustrate alignment of the guide tool bone screw attachment structure with the bone screw tool engagement structure.
Figure 42:
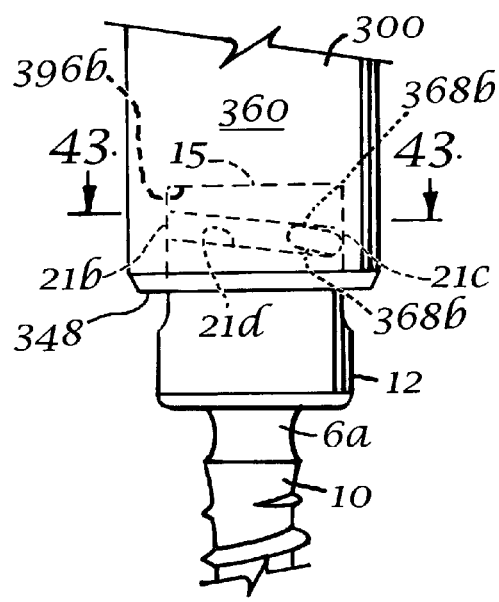
FIG. 42 is side view of the guide tool of FIG. 40, with portions broken away, showing the guide tool reversibly attached to the polyaxial bone screw.
Figure 41:
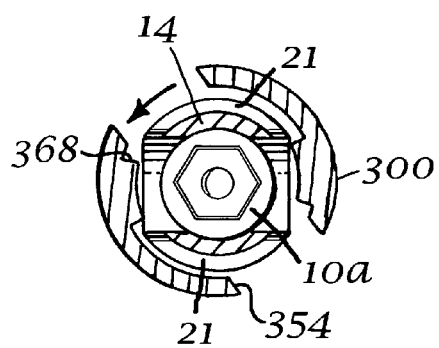
FIG. 41 is a cross-section of the guide tool and bone screw of FIG. 40 taken along line the 41-41 of FIG. 40 illustrating an initial step in aligning and engaging the guide tool bone screw attachment structure with the complementary bone screw tool engagement structure.
Figure 43:
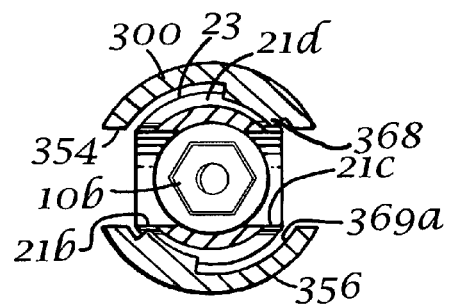
FIG. 43 is a cross-section of the guide tool and bone screw of FIG. 42 taken along line the 43-43 of FIG. 42 showing the guide tool bone screw attachment structure reversibly engaged with the bone screw tool engagement structure.
Figure 44:
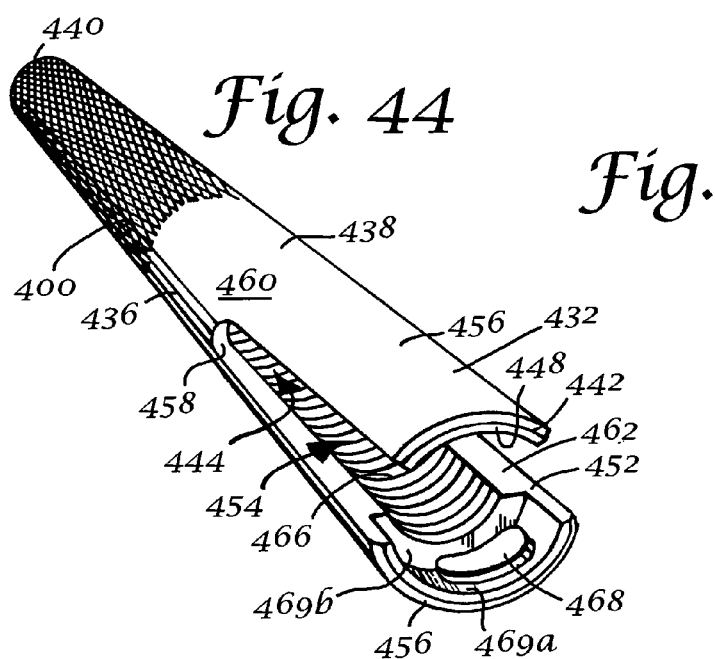
FIG. 44 is perspective view of a guide tool for percutaneously implanting a rod in a patient, in a fourth embodiment.
Figure 45:
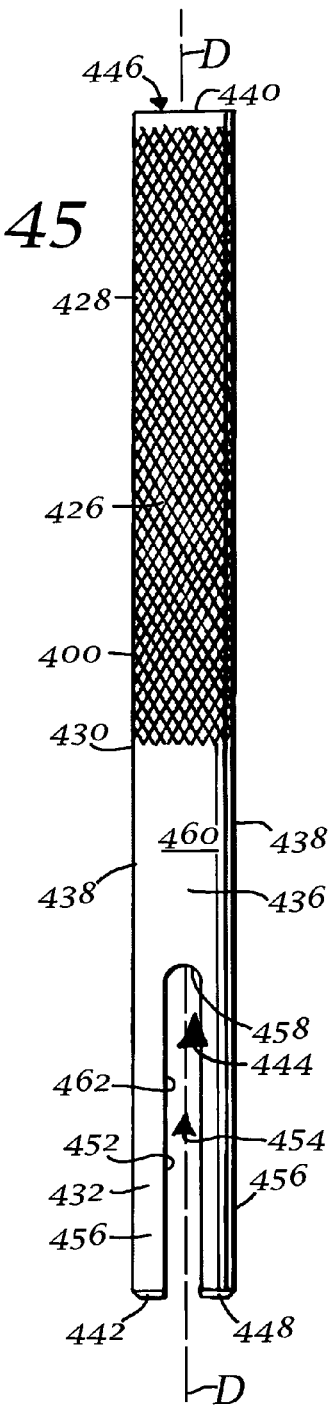
FIG. 45 a reduced side view of the guide tool of FIG. 44.
Figure 46:
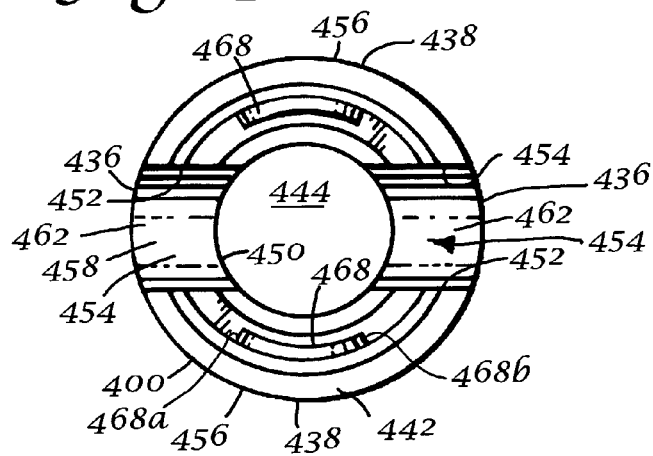
FIG. 46 is an enlarged bottom view of the guide tool of FIG. 44.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

FIGS. 1-25 illustrate a first embodiment of a guide tool, denoted by the numeral 100, for use in installing an orthopedic spinal rod 4 into a bone screw 6 in accordance with the present invention. The guide tool 1 is generally one of a plurality of such tools in a set of tools for installing the rod 4 into several bone screws 6. Depending upon the particular application, the tool set may include none, one or many guide tools 1 of the present invention in addition to none, one or many additional alternative tools (not shown), such as but not limited to intermediate and end guide tools, rod pushers, anti-torque tools, drivers, and the like, such as are described in U.S. Pat. Nos. 7,160,300, 7,651,502, 7,621,918, 7,862,587, 8,066,739, 8,100,915, 8,152,810, each of which is incorporated by reference herein in its entirety. The bone screws and guide tool are adapted to be used together and have complementary mating structures by which to be engaged and reversibly locked together. The bone screws 6 are implanted in the patent's spine and, in particular, in vertebrae 8 along the spine. Rods 4 are often installed on both sides of the spine, as is known in the art, during the same procedure.

With reference to FIGS. 5-25 and referring more specifically to the bone screw 6, each of the bone screws 6 includes a threaded shank 10 for screwing into and seating in a vertebra 8 that is part of the human spine, such as is known in the art. Each of the bone screws 6 also include a head 12, or receiver, with a pair of upstanding arms that have top surfaces 15 and define a rod receiving U-shaped channel 16 passing therethrough. The shank 10 may include an optional longitudinally extending cannula 11 that is sized and shaped to receive a guide wire or pin 11a therethrough to aid in implantation of the bone screw 6, such as is known in the art.

In some embodiments, the bone screw 6 is a polyaxial bone screw 6a, such as is shown in FIGS. 5-17. In other embodiments, the bone screw 6 is a monoaxial bone screw 6b, such as is shown in FIGS. 18-25, and which includes a fixed, non-movable head 12. In the case of polyaxial bone screws 6a, the shank 10 includes an upper portion 10a with a drive feature 10b that extends into the head 12 and is operationally secured therein, so that the head 12 is rotatable on the shank 10 until locked in position through engagement with the rod 4 under pressure. As shown in the illustrated embodiment shown in FIG. 10, the drive feature 10b is a hex-shaped upward projection adapted for engaging a driver with a complementary socket head, such as is known in the art. Additional or alternative drive features are foreseen. In particular, when the rod 4 is placed within an associated U-shaped channel 16, the rod 4 contacts or engages the drive feature 10b (see FIG. 15) and thereby urges the upper portion 10a downwardly whereby the upper portion 10a frictionally locks the shank 10 in position in a fixed angular position relative to the head 12. For example, FIG. 12 illustrates using the guide tool 1 to position the bone screw head 12 at an angle with respect to the shank 10. In some embodiments, the polyaxial bone screw 6a includes a pressure insert (not shown) that transfers a downward forced from the rod 4 to the bone screw upper portion 10a, so as to lock the position of the head 12 relative to the shank 10. It is foreseen that the bone screw 6 may include an upper pressure insert (not shown). Many different conventional bone screws where the head locks relative to the shank are well known in the art. It is noted that the monoaxial bone screw 6b also includes a drive feature 10b such as but not limited to a slot-shaped region sized and shaped to releasably engage a flat-head driver (not shown), such as is known in the art.

The present invention is not intended to be restricted to a particular type of bone screw. In the present embodiment, a polyaxial type bone screw 6a is utilized wherein the shank 10 is locked in position by direct or indirect contact with the rod 4. It is foreseen that a tool set including the guide tool 1 of the present invention can be used with virtually any type of bone screw, including polyaxial bone screws 6a of many different types wherein the head 12 is locked relative to the shank 10 by structure other than in the manner described in the illustrated embodiment, and also including monoaxial bone screws 6b and hooks.

Referring to FIGS. 6 and 18, each bone screw head 12 has a pair of upstanding arms 14. The upstanding arms each include an upper surface 15 and define a U-shaped rod-receiving channel, generally 16. The arms 14 include inner surfaces 18 with an internal guide and advancement structure, feature, portion or member 20 (see FIG. 5) thereon. The arms 14 each include an off-axis or circumferentially located tool engagement structure 21, also referred to as an engagement structure, portion or member, such as but not limited to a slot-like structure, channel or bore, that extends at least partially circumferentially about the periphery of the arms 14. While the tool engagement structure 21 of the illustrated embodiment is located on the arms 14, an attachment structure for this purpose could be located anywhere on the bone screw head 12. The bone screw's tool engagement structure 21 is sized, shaped and positioned so as to reversibly receive, engage or mate with a complementary engagement structure of the guide tool 1, which is described below.

A closure top 22 adapted for use with the bone screw 6 is received in the U-shaped channel 16, so as to lock the rod 4 therein. When the bone screw is a polyaxial bone screw 6a, locking the closure top 22 in the U-shaped channel 16 also locks the head 12 in place at a selected angle relative to the shank 10, such that the head 12 is substantially stationary or immobilized.

Referring to FIGS. 4, 5, 34 and 35, the closure top 22 includes top, bottom and side surfaces 22a, 22b, 22c, respectively, and at least one drive feature or imprint 22d. In the illustrated embodiment, the drive feature 22d includes a recessed slot member 22e and a pair of spaced pin engagement bores 22f. The pin engagement bores are separated by a bridge portion 22g and join the top and bottom surfaces 22a and 22b. Accordingly, the closure drive feature 22d is engaged by the driver 23, such as is shown in FIGS. 4 and 5, or alternatively by a flat-head screw driver. Alternative drive features 22d are foreseen, such as but not limited to a hex-shaped break-off head (see FIG. 34). The closure side surface 22c includes a guide and advancement structure 22h that is complementary to the bone screw guide and advancement structure 20. The bottom surface 22b includes a rod engagement feature 22i, which may include one or more of a downwardly extending ring, ridge, point, detent, or knurl. The rod engagement feature 22i is adapted to bite, cut into or compress the rod 4 when the closure 22 is secured or locked in the U-shaped channel 16, thereby securing the rod 4 therein. Alternative rod engagement features 22i are foreseen.

Still referring to FIGS. 4, 5, 34 and 35, the closure drive feature 22d is reversibly engaged by a closure driver 23 that is sized and shaped to be received through the guide tool 1, such as is shown in FIGS. 5 and 35 and described below. The closure driver 23 includes a head member or portion 23a, or imprint engagement structure, that is complementary to the closure drive feature 22d. The closure driver 23 also includes a shaft 23b and a handle 23c. In an exemplary embodiment shown in FIGS. 4 and 5, the driver head 23a include a pair of spaced downwardly extending pin members 23d, or fingers, that are spaced apart a distance substantially equal to the width of the closure bridge portion 22g and are also sized and shape to be reversibly received into and optionally through the pin engagement bores 22f, such that the closure driver 23 can rotate or screw the closure 22 into the bone screw 6. In another exemplary embodiment shown in FIGS. 34 and 35, the head 23a includes a hex-shaped socket 23e that is adapted to reversibly engage a complementary mating hex-shaped break-off closure head or drive feature 22d. It is foreseen that other closures may be used in conjunction with the bone screw 6. Accordingly, a closure driver 23 for use with such a closure 22 includes a head 23a adapted to engage the drive feature or imprint 22d of the closure 22.

The bone screw head 12 also includes an exterior surface 24. Additional details of bone screws for use with the present invention can be found in U.S. Pat. No. 7,776,067, which is incorporated by reference herein.

Referring again to FIGS. 1-25, in a first embodiment the guide tool 1 of the present invention has a substantially cylindrical elongate body 26 that is sized and shaped to be sufficiently long to extend from an attached implanted bone screw 6 through an exterior of a patient's skin so as to provide an outwardly extending upper handle portion 28 that allows and provides for gripping by a surgeon during procedures utilizing the guide tool 1. In addition to the handle portion 28, the guide tool body 26 includes an intermediate or middle portion 30 and a lower portion 32 along the length thereof.

The body 20 includes front and rear walls 36 and side walls 38, wherein the walls 36 and 38 extend from a top or top end 40 to a bottom or bottom end 42 of the guide tool 1. A cylindrical through-bore, generally 44, or through-channel, extends axially through the guide tool body 26 so as to join a first or top opening, generally 46, located at the top end 40 with a second or bottom opening 48 located at the bottom end 42. The longitudinally extending through-bore 44 is coaxial with the guide tool longitudinal axis A, has a substantially smooth cylindrical inner surface 50 and is sized and shaped to receive therethrough at least the closure top 22 for closing the bone screw 6. Accordingly, the closure top 22 is adapted or sized and shaped for use with the guide tool 1. The through-bore 44 is also sized so as to receive there through a closure driver 23 (see FIGS. 4-5, 11 and 13-15), and optionally additional tools, such as but not limited to a bone screw driver 51 (see FIG. 11) and a guide wire 11a. It is noted that the bone screw driver 51 includes a head portion 51a adapted to engage the bone screw shank drive feature 10b, a shaft 51b, a handle 51c and optionally a longitudinally extending cannula 51d that extends longitudinally or axially upwardly from the head 51a, so as to join a cannula opening located in the driver's head portion 51a with an opening 51e located at the top of the handle portion 51c. The driver's cannula 51d receives the guide wire 11a and aids in positioning the bone screw 6. For example, when implanting the bone screw 6, the guide wire 11a is generally implanted in the vertebra 8. Then the guide tool 1 and the bone screw 6 are engaged with one another, and the bone screw 6 is placed over the guide wire 11a, such as through the cannula 11 in the bone screw shank 10, until the tip 10 of the shank contacts the vertebra 8. The driver 51 is then inserted through the guide tool 1 such that the head 51a engages the shank's drive feature 10b and the guide wire 11a is received through the driver's cannula 51d, such as is shown in FIG. 11. The driver 51 is then used to drive the shank 10 into the bone 8 by applying torque to the shank 10, such as is known in the art. After the bone screw 6 has been implanted into the vertebra 8, the driver 51 is removed from the guide tool 1, and the rod implantation procedure is continued, such as is known in the art.

The guide tool 1 includes a cutout portion, region or surface 52 that is located at or near the bottom 42, wherein a portion of each of the front and rear walls 36 of the through-bore 44 are removed in order to provide a slot-shaped region, generally 54, also referred to as a through-slot, rod-receiving member, portion or channel 54. The cutout portions 52 are parallel and opposed to one another and extend from the bottom longitudinally toward the intermediate portion 30 of the guide tool body 26. The through-slot 54 is substantially alignable with the bone screw U-shaped channel 16, and is also sized and shaped to allow passage of the rod 4 therethrough (see FIGS. 9-11, 13-15 and 21-22), such as is described below. The through-slot 54 extends through the front and rear walls 36 of the body 26, such that the side walls 38 form downwardly extending, spaced opposed legs, members or tangs 56. Thus, the body lower portion 26 includes the through-slot 54 and the legs 56. The cutout portion 52 includes an upper slot surface 58 that may be arch-shaped, U-shaped, planar or the like. In some embodiments, portions the body outer surface 60 adjacent to the through-slot openings 62 are beveled, slanted or partially conical, so as to guide, direct or assist in threading or passing an end of the rod 4 into the opening 62 of the through-slot 54.

At or near the bottom 38 of the body 26, the guide tool 1 includes a rod abutment recess or relief 64. The relief 64 is sized and shaped for the purpose of bridging the rod 4 when the guide tool 1 is rotated for removal, such as to twist the guide tool 1 off of the bone screw head 12, as described elsewhere herein (see FIGS. 16 and 23).

Also near the bottom 38 of the body 26, the guide tool's through-bore 44 includes a helically wound or partially helically wound guide and advancement structure 66 which may include conventional helical threads, helically wound square threads, a flange form, or other guide and advancement structure sized and shaped to cooperate with complementary equivalent or mateable structure within the bone screw head 12, such as for example the guide and advancement structure 20 on the bone screw arms 14 and the guide and advancement structure 22h located on the side 22c of the closure top 22. The tool guide and advancement structure 66 is located or adapted such that when the guide tool 1 is mounted on, engaged with or attached to the bone screw 6, such as when the through-slot 54 is substantially aligned with the U-shaped channel 16, such as is shown in FIGS. 9 and 10 for example, the closure 22 is smoothly and rotatably transferable from the guide tool through-bore 44 to the bone screw U-shaped channel 16.

The guide tool 1, of the first embodiment, includes at least one radially inward facing bone screw attachment structure 68, also referred to as a bone screw engagement structure or first attachment structure, that is located at or near the bottom opening 48. For example, as shown in FIGS. 1-4, 8 and 10, in the illustrated embodiment, the inner surface 50 of each leg 56 includes a bone screw attachment structure 68. Generally, the tool's bone screw attachment structure 68 includes at least one of a radially inwardly extending projection, flange, shoulder, shelf, arm, detent, hook member or the like on at least one of the leg the inner surfaces 50. As described in greater detail below, the tool's bone screw attachment structure 68 is sized, shaped and adapted to releasably and cooperatively engage or mate with a complementary attachment structure of the bone screw 6, whereby the guide tool 1 and the bone screw 6 are releasably locked together, which in turn facilitates alignment of the guide tool's through-slot 54 with the bone screw's U-shaped channel 16. It is noted that numerous complementary and cooperative sized, shaped and configurations of the guide too's bone screw attachment structure 68 and the bone screw's tool engagement structure 21 are foreseen. Additionally, at least a portion of these structures 68 and 21 may be located elsewhere on the respective structure 1 or 6.

To facilitate engagement between the bone screw's tool engagement structure 21 and guide tool's screw attachment structure 68, the guide tool 1 also includes a mating chamber, cup, portion or area 69. This mating chamber 69 is sized and shaped to receive therein at least an upper portion of the bone screw head 12, such as but not limited to the bone screw's arms 14, and further to reversibly engage the tool engagement structure 21 located on the exterior surface 23 of the bone screw arms 14. In the exemplary embodiment shown in FIG. 1, the mating portion 69 includes a discontinuous cylindrical inner chamber 69a, a pair of crescent-shaped planar screw abutment surface 69b, and the radially inwardly facing attachment structure 68. Alternatively shaped mating portions 169 are foreseen.

Referring to FIGS. 6-8, when the guide tool 1 is mounted on a bone screw head 12, the mating portion 69 extends downwardly around a portion of the head 12, or receives the bone screw arms 14 therein, such that the mating portion's screw abutment surfaces 69b contact or abut the arm top surfaces 15. Additionally, the inner chamber surface 69c contacts the bone screw arm 14 exterior surfaces 23. Initially, as shown in FIGS. 7 and 8, the guide tool's bone screw attachment structure 68 is vertically aligned with but not engaged with the bone screw's tool engagement structure 21. When in this configuration, the guide tool's through-slot 54 is not aligned with the bone screw's U-shaped channel 16. As shown in FIGS. 9 and 10, the attachment structure 68 and the engagement structure 21 are cooperatively mated together by rotating the guide tool 1 counter-clockwise relative to the bone screw head 12. In the illustrated embodiment, the amount of rotation is about 90-degrees. This rotation slides the tool's screw attachment structure 68 into the bone screw's tool engagement structure 21, whereby the structures 68 and 21 are reversibly and cooperatively interlocked or mated, such that the guide tool 1 and the bone screw 6 are reversibly locked together. When engaged in this manner, the guide tool 1 may be said to be mounted on the bone screw 6.

It is noted that the bone screw's tool engagement structure 21 includes a stop or abutment surface 21a. The tool's screw attachment structure 68 includes another stop or abutment surface 68a, also referred to as a leading surface, that is adapted to cooperatively engage the stop 21a. When the guide tool's screw attachment structure 68 is mated with the bone screw's tool engagement structure 21, the respective abutment surfaces 68a and 21a cooperatively abut or engage one another, thereby preventing further rotation of the guide tool 1 with respect to the bone screw head 12. Accordingly, this abutment of the surfaces 68a and 21a ensures that the guide tool 1 is not over-rotated, so that the tool's through-slot 54 and the bone screw's U-shaped channel 16 are substantially aligned, such as is shown in FIGS. 9-10. It is foreseen that the attachment and engagement structures 68 and 21, respectively can be sized and shaped such that the amount of rotation required to alight the through-slot 54 with the U-shaped channel 16 may be somewhat larger or smaller the 90-degrees. When the through-slot 54 and the U-shaped channel 16 are substantially aligned, a rod 4 and a closure 22 can be moved, passed, transferred or slid from the guide tool 1 to the attached bone screw 6.

Alternative structures and methods for engaging or mounting the guide tool 1 and the bone screw 6 together are foreseen. For example, in some embodiments, the bone screw's tool engagement structure 21 includes additional locking structure that enables locking the guide tool 1 with the bone screw 6 by pulling the guide tool 1 slightly axially upward relative to the respective bone screw 6.

The guide tool 1 is disengaged from the bone screw 6 using a twist-off maneuver, wherein the guide tool 1 is rotated 90-degrees clockwise from an attaching configuration, such as is described above, when viewing from the top so as to disengage the guide tool's screw attachment structure 68 from the bone screw's tool engagement structure 21 (e.g., see FIGS. 15-17). In some instances, the guide tool 1 is rotated somewhat more or less than 90-degrees to make the necessary alignment for removal, which depends on the specific construction of the parts.

In this manner, the guide tools 1 twists off of respective bone screws 6 and in the particular illustrated embodiment the guide tools 1 are also assembled on the bone screws 6 by the opposite twist-on maneuver, which is the reverse of the twist-off maneuver. In certain embodiments where there is enough flexibility in the legs 56, such that the legs 56 can be splayed radially outwardly at the bottom 42 thereof, so the guide tool 1 snaps-on over the bone screw 6.

Referring now to FIGS. 16 and 17, the space 54 between the guide tool legs 56 that is equivalent to the width of the through-slot's opening 62 is preferably substantially equivalent to the space between the bone screw's arms 14 so that the through-bore 44, or the slot-shaped region 54, aligns with the U-shaped channel 16 when the guide tool 1 is mounted on a respective bone screw 6. The guide tool's rod-abutment recess 64 is sized, shaped and positioned such that when the rod 4 is located, fixed, implanted or installed in the bone screw 6, the guide tool 1 can rotate about the tool's longitudinal axis A and the rod-abutment recess 64 allows the guide tool 1 to straddle over the rod 4, thereby allowing the guide tool 1 to twist relative to the bone screw 6 and free the guide tool's bone screw attachment structure 68 from the bone screw's tool engagement structure 21 and thereafter be removed after all procedures are complete, as described below. Without such a rod-abutment recess 64, when the guide tool 1 was rotated clockwise for disconnection from the bone screw 6, movement of the legs 56 would be blocked or hindered by the rod 4. As a result, the guide tool 1 would likely have to be pried off of the bone screw 6, so as to be removed therefrom.

Closure top 22, also referred to as an enclosure, closes between the spaced bone screw arms 14 so as to secure the rod 4 in the channel 16. The closure top 22 can be any of many different plug type closures known in the art. Preferably the closure top 22 has a cylindrical body that has a helically wound mating closure guide and advancement structure 22h. The closure's guide and advance at structure 22h can be of any type, including V-type threads, buttress threads, reverse angle threads, or square threads. Preferably the closure's guide and advancement structure 22h is a helically wound flange form that interlocks with a reciprocal flange form as part of the guide and advancement structure 20 on the interior of the bone screw arms 14. A suitable locking guide and advancement structure of this type is disclosed in U.S. Pat. No. 6,726,689, which is incorporated herein by reference. Referring to FIGS. 4-5, the guide tool's helical wound guide and advancement structure 66, which is located in the lower portion 32 of each of the guide tools 1, is sized and shaped to receive the mating guide and advancement structure 22h of the closure top 22. When the U-shaped channel 16 and the through-slot 54 are aligned, the bone screw's guide and advancement structure 20 forms a generally continuous helically wound pathway with the tool's guide and advancement structure 66, but does not require locking between the closure top 22 and the tool 1, even when a locking flange form is utilized on the closure top 22. Further, when the U-shaped channel 16 and the through-slot 54 are aligned, can be rotatably passed between the guide tool 1 and the bone screw 6, such as is shown in FIG. 5. This enables the rod 4 to be reduced into and seated in the U-shaped channel 16 using the closure top 22 and the associated closure driver 23, such as is shown for example in FIGS. 13-15.

Referring to FIGS. 4, 5, 13, and 34-35, in the illustrated embodiment, the closure's guide and advancement structure 22h has a square form or a square thread type shape. The guide tool's guide and advancement structure 66 allows the closure top 22 to be rotated and the surgeon to develop mechanical advantage to urge or drive the rod 4, while still outside the bone screw head 12, toward and into the bone screw head 12, such as is shown in FIGS. 13-15. Alternatively, this configuration enables pulling the bone screw head 12 around the rod 4 by rotating the closure top 22 in the guide tool 1. This is especially helpful where the rod 4 is bent relative to the location of the vertebra 8 to which the rod 4 is to be attached and is not easily placed in the bone screw head 12 without force and the mechanical advantage provided by the guide and advancement structure 66. In particular, the guide tool's guide and advancement structure 66 is located and positioned to align with the guide and advancement structure 20 on the insides 18 of the bone screw arms 14, as seen in FIGS. 5 and 35 and pass the closure top 22 therebetween while allowing the closure top 22 to continue to rotate and to continuously apply force to the rod 4, so as to seat the rod 4 in the bone screw head 12.

Referring to FIGS. 34-35, in some embodiments, the closure top 22 includes a break off head 22d that breaks from the body in a break off region upon the application of a preselected torque, such as about 95 inch-pounds. The break off head 22d preferably has a hexagonal cross section faceted exterior that is adapted to mate with a cooperating hex-shaped socket 23e (shown in phantom) of the driver head 23a. In other embodiments, the closure top 22 may include an imprint 22d adapted to cooperate with a flat-head closure driver 23. It is foreseen that different driving heads 23a or other methods of driving the closure top 22 can be utilized with certain embodiments of the invention. For example, the closure top 22 may have an axial imprint 22d or engagement structure adapted to releasably engage a complementary driving head 23a of the closure driver 23.

As is known in the art, additional tools may be utilized to assemble the implant. For example, a rod pusher (not shown) that has an elongate shaft or rod that is received in and passes through the interior of the guide tool 1, such as the through-bore 44 of the guide tool 1, can be used to engage and urge the rod 4 downward. Alternatively, a pusher or gripper (not shown) of the type that operates outside the guide tool 1 can be utilized.

FIGS. 4-5, 11, 13, 15, and 34-35 illustrate closure installation tools 23 or drivers. Each of the tools 23 has an elongate rod or shaft 23b adapted to be received in and pass axially through the guide tool through-bore 44 and a handle 23c. The lower end of the rod 23b terminates in either a driving engagement structure 23d, such as a socket 23c, shaped head 23a or an imprint engagement structure 23d, that is adapted to engage a respective complementary engagement structure of the closure 22, such as is described above.

Another tool useful in implanting a rod 4 is an antitorque tool (not shown) which is preferably used with the closure installation tool 23 to torque and set the closure top 22, so it is snug against the rod 4, and thereafter break away the break off head 22d. The antitorque tool may include a tubular hollow shaft that is sized and shaped to be slidably received over the guide tool 1. The antitorque tool has a lower end that has a pair of diametrically spaced bridges. Each of the bridges is sized and shaped to fit over the rod 4. When in place, the antitorque tool allows a surgeon to counter torque applied by the closure installation tool 23, when applying torque to and breaking away the break off head 22d.

In use, the previously described tools are utilized to attach one or more rods 4 to the human spinal column.

The minimally invasive implantation procedure (not shown) is begun by forming a relatively small incision in the skin for each bone screw 6 to be used. The incisions are stretched into a round shape with a circumference equal to or just slightly larger than the guide tools 1. The skin is relatively flexible and allows the surgeon to move the incision around relative to the spine to manipulate the various tools and implants, as required. A drill is utilized to form a guide bore in a vertebra 8 under guidance of non-invasive imaging techniques, which procedure is well known and established. A thin pin or wire 11a is inserted in the guide bore, such as for example as is shown in FIG. 11. A bone screw 6 is selected in accordance with the size of the patient's vertebra 8 and the requirements of the spinal support needed. Bone screws 6 having a rotatable or poly axial head 12, such as is shown in FIG. 12, are preferred for the procedure, as they allow relatively easy adjustment of the rod 4 in the guide tools 1 during placement and for movement of tools 1, as described below. The bone screw 6 is also cannulated 11 so as to be receivable over and guided by the pin or wire 11a toward the proper position in the associated vertebra 8.

Before placing the bone screw 6 in the vertebra 8, the bone screw 6 is preferably joined to an associated guide tool 1. This could be done after insertion of the bone screw 6, but it is preferred to assemble both before inserting the bone screw 6. The guide tool 1 is rotatably attached to the bone screw head 12 between the legs 56, using a twist-on procedure, such as is described above and shown in FIGS. 6-9. Namely, the guide tool 1 can be axially rotated ninety degrees relative to the bone screw 6 and the attachment structure 68 aligned with the bone screw's tool engagement structure 21, such as is described above.

A series of bone screws 6 are installed in each vertebra 8 to be attached to the rod 4 by use of a screwdriver or installation tool 51, that has a head 51a designed to grip the particular bone screw 6 used and which is also cannulated 51d to receive the pin or guide wire 11a. For each bone screw 6, an associated guide tool 1 extends through the skin. A guide tool 1 is located at each end of the series of bone screws 6 as well as on each intermediate bone screw 6. The guide tools 1 are turned or rotated so the through-slots 54 face one another so as to provide a continuous path adapted to receive the rod 4 therethrough.

The rod 4 is then inserted diagonally through one of the end skin incisions so that a first rod end passes through the through-slots 54 in the guide tools 1. Back muscle tissue separates easily here to allow the insertion of the rod 4 and can be further separated by finger separation or cutting through one of the incisions, if required.

Once the rod 4 is positioned in the guide tools 1, a closure top 22 and closure driver 23 are utilized to push the rod 4 in each guide tool 1 toward the bone screw 6 associated with the guide tool 1 until the rod 4 is seated in the bone screw U-shaped channels 16, such as is shown in FIGS. 5, 13-15 and 35. When the rod 4 is at the bottom of the guide tools 1, such as seen in FIG. 15, the guide tools 1 can be manipulated to further align the bone screw heads 12 relative to the rod 4 prior to tightening and torquing the closure tops 22.

Because the rod 4 is normally bent and/or the vertebrae 8 do not align properly, the rod 4 must normally be biased into the bone screw heads 12. This is accomplished by using the closure installation tool 23 in the manner illustrated in FIGS. 5, 13-15 and 35, as is described above. In particular, the closure installation tool 23 has a socket or imprint engagement structure 23d that grips the closure top 22. The installation tool 23 with closure top 22 therein is placed in the guide tool's elongate through-bore 44, or top to bottom channel, through the top opening 46 in guide tool 1. The closure top 22 is then driven under manual control of the surgeon by use of the installation tool 23 toward the rod 4. Near the bottom end 42 of the guide tool 1, such as near the bottom opening 48 of guide tool 1, the guide and advancement structure 22h of the closure top 22 engages the guide tool's helical wound guide and advancement structure 66, and the tool 23 and closure top 22 are rotated so as to drive the closure top 22 downward against the rod 4 and to urge the rod 4 into the bone screw U-shaped channel 16. At the bottom of the guide tool 1, the closure top guide and advancement structure 22h engages and begins to mate with the guide and advancement structure 20 on the arms 14 of the respective bone screw 6, and continued rotation of the tool 23 drives the rod 4 downward and into engagement with the bone screw shank upper portion 10a, so as to snug against and frictionally lock the shank 10 in position relative to the bone screw head 12. It is noted that in some embodiments, the bone screw 6 includes a pressure insert located between the rod 4 and the shank upper portion 10a.

Once all of the closure tops 26 are in final seating position in respective bone screws 6 and the surgeon is satisfied with the position of all of the elements, the antitorque tool (not shown) is mounted over each guide tool 1 with the bridges straddling the rod 4 to prevent rotation. The closure installation tool 23 is inserted in the associated guide tool 1 and engaged with the closure tops 22. By cooperative use of the anti-torque tool and the closure driver 23, a preselected torque is manually applied to the closure top 22. If the closure top 22 includes a break-off head 22d, the break-off head 22d is removed during this procedure.

The guide tools 1 are then detached from the respective bone screws 6, using the twist-off procedure described above. Namely, each guide tool is rotated ninety degrees clockwise (see FIGS. 16-17 and 23-25) so that the recess 64 straddles the rod 4 (see FIGS. 16 and 23) to allow respective tool and screw attachment structure 68 and 21 to detach or disengage from one another. The guide tool 1 is then pulled axially upward away from the bone screw 6, such as is shown in FIGS. 17 and 24, and from the incision in the skin, after which the incision is closed. It is foreseen that the guide tool 1 and the bone screw 6 may be configured or adapted such that the guide tool 1 is mountable onto the bone screw with a clockwise twist-on procedure and disconnectable with a counter-clockwise twist-off procedure.

FIGS. 26-35 illustrate a guide tool 200 in a second embodiment. The guide tool 200 is similar to the guide tool 1 of the first embodiment, the description of which is incorporated herein by reference. Accordingly, structures corresponding between the two embodiments have been numbered similarly.

In a second embodiment, the guide tool 200 includes an elongate body 226 having an upper handle portion 228, an intermediate or middle portion 230, a lower or bottom portion 232 and a longitudinally extending axis B. The body 226 is generally cylindrical and includes front and rear walls 236 and side walls 238, and top and bottom ends 240 and 242, respectively. A through-bore 244 extends longitudinally through the body 226 and joins a first, upper or top opening 246 located at the tool top end 240 with a second, lower or bottom opening 248 located at the tool bottom end 242. The through-bore 244 is adapted to receive a closure driver 23, a closure 22 and a bone screw driver 51 therein. In preferred embodiments, the through-bore 244 is coaxial with the longitudinal axis B, such as is shown in FIG. 27.

At the lower end 242, the front and rear walls 236 each include an upwardly extending cutout 252. The cutouts 252 extend upwardly from the bottom opening 248 to or near to the body middle portion 236. For example, the cutouts 252 may extend upwardly a length of about 0.25-percent to about 0.5-percent of the total length of the guide tool 200, so as to provide legs 256 of increased or extended length relative to the legs 56 of the first guide tool 1. This increased leg length can provide additional flexibility to the legs 256, so as to enable the legs 256 to expand apart and snap onto the bone screw 6. Also, given the tight working area of the minimally invasive incision, the extra length of the cutouts 252, as compared with the cutouts 52 of the first embodiment, provides additional space for passing or installing a rod 4 simultaneously through the patient's skin and through the cutouts 252. This makes the installation somewhat easier than with the guide tool 1 of the first embodiment and may reduce the amount of tissue resection required for the surgical procedure.

The cutouts 252 define a through-slot 254 and the pair of spaced opposed legs 256. Each cutout 252 includes an upper slot surface 258. The body outer surface 260 is joined with the through-bore inner surface 250 by spaced opposed openings 262. The openings 262 include sides 263 that run substantially parallel with one another and are spaced a distance equal to or slightly great that a diameter of the rod 4. This sizing allows the rod 4 to be smoothly threaded through the through-slot 254, optionally while holding the rod 4 in a somewhat more vertical orientation relative to the surgical incision. As a result, a smaller incision can be used for the surgical procedure.

The legs 256 each include a rod-abutment recess, cutout or relief 264 that is sized and shaped to allow the surgeon to perform the twist-off maneuver described above, after the rod 4 has been installed in that bone screw 6.

As shown in FIG. 34, the guide tool inner surface 250 includes a helically wound guide and advancement structure 266 substantially similar to the guide and advancement structure 66 of first guide tool 1. Generally, the guide and advancement structure 266 runs from above the cutout upper surface 258 to the mating portion 269 at the lower end 232 of the guide tool body 226. However, it is foreseen that the guide and advancement structure 266 may begin somewhat higher or lower than is shown in the figures. For example, it is foreseen that the guide and advancement structure 266 may extend to nearly the top 240 of the guide tool 200, or, alternatively, may begin below the upper slot surface 258. The guide and advancement structure 266 is adapted to cooperatively rotatably mate with the closure's guide and advancement structure 22h. As shown in FIG. 35, when the guide tool 200 is mounted on the bone screw 6, the guide tool's guide and advancement structure 266 is configured to align with the bone screw's guide and advancement structure 20, such that the closure top 22 can be smoothly rotatably passed between the two structures.

Referring now to FIGS. 29-33, as shown in FIGS. 30 and 31, when initially mounting the guide tool 200 on top of the bone screw head 12, the guide tool 200 is placed on top of the bone screw head 12 in such an orientation that the guide tool's screw abutment surfaces 269 contact the bone screw arm top surfaces 15 but the guide tool's through-slot 254 and the bone screw's U-shaped channel 16 are not aligned. When in this configuration or position, guide tool's lozenge-shaped bone screw attachment structure 268 (shown in phantom in FIG. 30) is vertically aligned with the bone screw's tool engagement structure 21 (shown in phantom in FIG. 30).

As shown in FIG. 31, in the illustrated embodiment, the guide tool engagement structure 276 is generally shaped like a rectangle with rounded corners or like a lozenge. The bone screw's tool engagement structure 21 is a complementary sized and shaped channel or slot adapted to slidingly receive therein and cooperatively mate with the attachment structure 268, such that the two structures 268 and 21 snugly engage one another. The opening 21b of the engagement structure 21a is contiguous with the U-shaped channel 16, such that the counter-clockwise rotation of the guide tool 200 with respect to the bone screw head 12 slides the attachment structure 268 into the tool engagement structure 21, until the stops 268a and 21a abut one another. Alternatively shaped structures 268 and 21 are foreseen, so long as the structures 268 and 21 are complementary to one another and cooperatively reversibly engage, or interlock, with one another using a twist-on motion.

It is noted that when viewed from the side 238, the attachment structure 268 is located very closed to the left-hand edge of the respective leg 256, just above the rod-abutment surface 264. This arrangement of structures enables the guide tool 200 to be twisted onto the bone screw 6 using a counter-clockwise turn (compare FIGS. 31 and 33). It is foreseen that the guide tool's bone screw attachment structure 268 and the rod-abutment surface 264 could be located on the opposite or right-hand side to the leg 256, as denoted by the asterisk (*) in FIG. 31, such that the guide tool 200 would be twisted onto the bone screw 6 using a clockwise turn. Additional alternative configurations are foreseen.

Referring again to FIGS. 29-33, once the guide tool's attachment structure 268 and the slot or bone screw's engagement structure 21 are aligned (see FIGS. 30 and 31) the guide tool 200 is rotated about 90-degrees counter-clockwise, relative to the bone screw 6. During this twisting movement, the attachment structure 268 enters and engages the engagement structure 21, such as is shown in FIG. 33.

As noted above, the bone screw engagement structure 21 includes a stop surface 21a that during the twist-on maneuver come into contact with or engagement with a first or forward surface 268a of the attachment structure 268, such that the guide tool 200 cannot be rotated farther. When the forward surface 268a engages the stop surface 21a, the guide tool's through-slot 254 is substantially aligned with the bone screw's U-shaped channel 16. Additionally, when forward surface 268a and the stop surface 21a are in engagement, the tool's guide and advancement structure 266 is correctly aligned with the bone screw guide and advancement structure 20, so as to provide a smooth transition therebetween, such that the closure top 22 can be installed into the bone screw 6 without binding up (see FIG. 35).

FIGS. 36-43 illustrate a guide tool 300 in a third embodiment. The third guide tool 300 is substantially similar to the guide tools 1 and 200 of the first and second embodiments, the descriptions of which are incorporated herein by reference. Therefore the guide tool 300 is numbered in a similar manner to guide tools 1 and 200. In particular, the guide tool 300 of the third embodiment includes the following structures, portions or features: a body 326 that includes an upper handle portion 328, an intermediate portion and a lower portion 332, front and back walls 336, side walls 338, top and bottom ends 340 and 342 respectively, a through-bore 344 that is coaxial with the longitudinal axis C and extends from a top opening 346 located at the top end 340 to a bottom opening 348 located at the bottom end 342. The through-bore 344 includes an inner surface 350. Cut-outs 352 in the front and back walls 336 form a through-slot 354 that extends longitudinally upward from the bottom opening 348 and is joined with the through-bore 344. The through-slot 354 also divides the lower portion 332 of the body 326 into a pair of spaced opposed legs 356. The through-slot 354 includes an upper surface 358 and openings 362. The openings 362 join the through-bore inner surface 350 with the body outer surface 360. Similar to the guide tools 1 and 200 of the first and second embodiments, the body lower portion 332 includes a rod-abutment relief 364 that is adapted to straddle a rod 4 during a twist-off procedure, such as is described above. The guide tool 300 also includes a guide and advancement structure 366 adapted for use with a closure top 22, a radially inwardly facing bone screw attachment structure 368 with at least one camming surface 368b, and a mating chamber 369 for engaging the bone screw 6. The mating chamber 369 includes a chamber inner surface 369a and screw abutment surfaces 369b similar to those described with respect to guide tool's 1 and 200.

The bone screw attachment structure 368 of the guide tool 300 is substantially different from the attachment structures 68 and 268 of the first and second guide tool 1 and 200, respectively. Namely, instead of the having an attachment structure that is generally perpendicularly oriented relative to the longitudinal axis, such as the attachment structure 268, the third guide tool's radially inwardly facing bone screw attachment structure 368 is an inwardly extending or facing camming structure with camming surfaces 368b. As is most easily seen in FIGS. 38 and 42, the guide tool's bone screw attachment structure 368 is slanted relative to the longitudinal axis C. In particular, the attachment structure 368 is a sloped rectangular structure with rounded corners, wherein the structure 368 slants upwardly from the edge of the respective leg 356 toward the screw abutment surface 39b of the tool's mating chamber 369.

As shown in FIGS. 40-43, the bone screw 6 is adapted to cooperatively engage the guide tool 300. Accordingly, the bone screw's tool engagement structure 21 sized and shaped to cooperate with the guide tool's bone screw attachment structure 368. In the illustrated embodiment, the tool engagement structure 21 is a partially helically wound slot or channel with upper and lower openings 21b and 21c, respectively, and at least one camming surface 21d. The tool engagement structures 21 wraps around the outer surfaces of the respective arms 14 such that the upper openings 21b are located closer to the respective arm top surfaces 15 than are the lower openings 21c. The bone screw's tool engagement structure 21 is sized and shaped to slidingly receive the guide tool's bone screw attachment structure 368 therein using a counter-clockwise twist-on maneuver. For example, when the guide tool 300 is mounted on the bone screw 6, counter-clockwise rotation of the guide tool 300 with respect to the bone screw head 12 slides the attachment structure 368 into the upper opening 21b of the engagement structure 21. Upon entry of the attachment structure 368 into the engagement structure 21, the guide tool's screw abutment surfaces 369b, of the tool's mating chamber 369, are spaced from the bone screw's arm upper surfaces 15. Additionally, the camming surfaces 368b and 21d engage one another. Upon continued clockwise rotation of the guide tool, the camming surfaces 368b and 21d cooperate to lock the guide tool's mating chamber 369 about the upper portions of the bone screw arms 14. When the guide tool's through-slot 354 is substantially aligned with the bone screw's U-shaped channel 16, the surfaces 369b and 15 engage one another, whereby additional counter-clockwise rotation of the guide tool 300 is prevents. However, it is foreseen that if over-rotation occurs, the guide tool 300 can be rotated clockwise to align the through-slot 354 and the U-shaped channel 16. Disconnection of the guide tool 300 from the bone screw 6 is generally accomplished using a clockwise twist-off procedure, such as described elsewhere herein. It is foreseen that the guide tool 300 and the bone screw 6 can be configured and arranged for a clockwise twist-on procedure and a counter-clockwise twist-off procedure. It is also foreseen that the guide tool legs 356 may include sufficient flexibility enable some splaying apart, so as to assist in mounting the tool 300 on the bone screw 6.

FIGS. 44-51 illustrate a guide tool 400 in a fourth embodiment. The fourth guide tool 400 is substantially similar to the guide tools 1, 200 and 300 of the first, second and third embodiments, the descriptions of which are incorporated herein by reference. Therefor the guide tool 400 is numbered in a manner similar to the numbering of the guide tools 1, 200 and 300. In particular, the guide tool 400 of the fourth embodiment includes the following structures, portions or features: a body 426 that includes an upper handle portion 428, an intermediate portion and a lower portion 432, front and back walls 436, side walls 438, top and bottom ends 440 and 442 respectively, a through-bore 444 that is coaxial with the longitudinal axis D and joins the top opening 446 located at the top end 440 with the bottom opening 448 located at the bottom end 442. The through-bore 444 includes an inner surface 450. Cut-outs 452 in the front and back walls 436 form a through-slot 454 that extends longitudinally upward from the bottom opening 448 and is joined with the through-bore 444. The through-slot 454 also divides the lower portion 432 of the body 426 into a pair of spaced opposed legs 456. The through-slot 454 includes an upper surface 458 and openings 462. The openings 462 join the through-bore inner surface 450 with the body outer surface 460. In contrast to the guide tools 1, 200 and 300 of the first, second and third embodiments, the body lower portion 432 does not include a rod-abutment relief. Instead, as described in greater detail below, the guide tool's mating chamber 469 is adapted such that a rod-abutment relief is not required for disconnection of the guide tool 400 from and attached bone screw. The guide tool 400 includes a guide and advancement structure 466 adapted for use with a closure top 22, a radially inwardly facing bone screw attachment structure 468 and a mating chamber 469 for engaging the bone screw 6. The mating chamber 469 includes a chamber inner surface 469a and screw abutment surfaces 469b.

As is most easily seen in FIGS. 44 and 46-51, the guide tool's bone screw attachment structure 468 is located on the mating chamber's inner surface 469a approximately equidistant from each of the cutouts 4521 theat define the legs 456. Additionally, the attachment structure 468 is located very near to or adjacent to the lower opening 468 or the bottom 442 of the respective leg 456. Consequently, the tool's mating chamber 469 is very short relative to the mating chambers 69, 269 and 369 described above.

Figure 47:
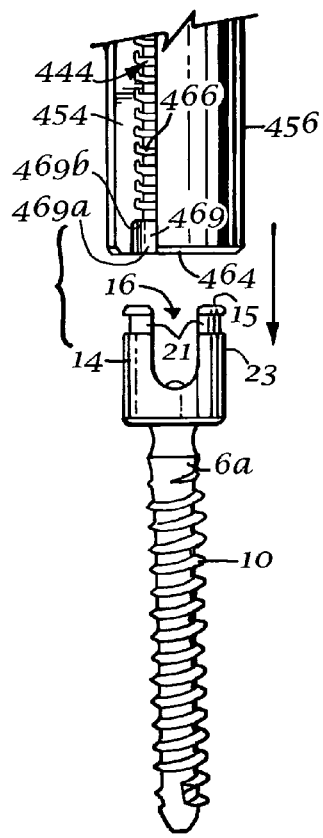
FIG. 47 is an enlarged side view of the guide tool of FIG. 44, with portions broken away, illustrating a first step in attaching the guide tool of FIG. 44 to a polyaxial bone screw adapted for use therewith.
Figure 48:
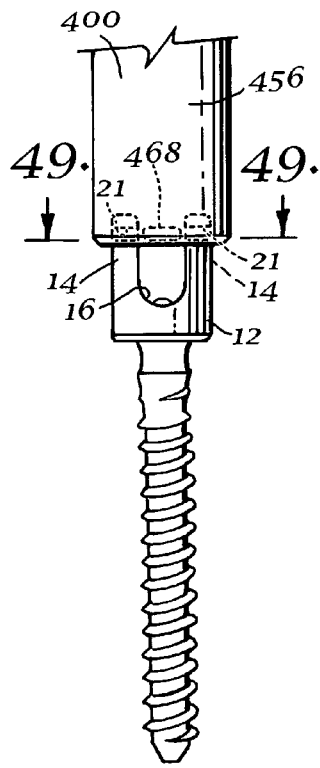
FIG. 48 is a side view of the guide tool of FIG. 47 illustrating a further step in attaching the guide tool to the polyaxial bone screw, wherein the guide tool through-slot is not yet aligned with the bone screw U-shaped channel.
Figure 50:
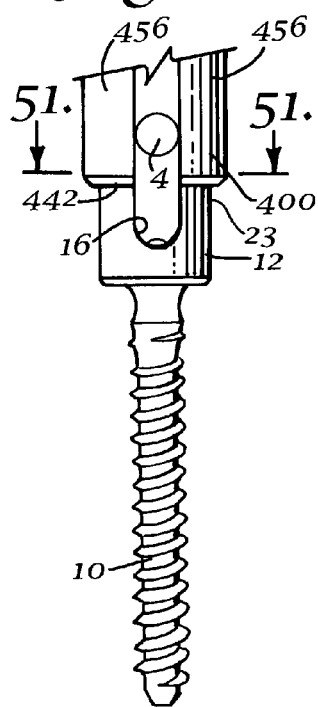
FIG. 50 is a side view of the assembly of FIG. 48 illustrating attachment of the guide tool to the polyaxial bone screw of FIG. 47, wherein the guide tool through-slot is substantially aligned with the bone screw U-shaped channel.
Figure 49:
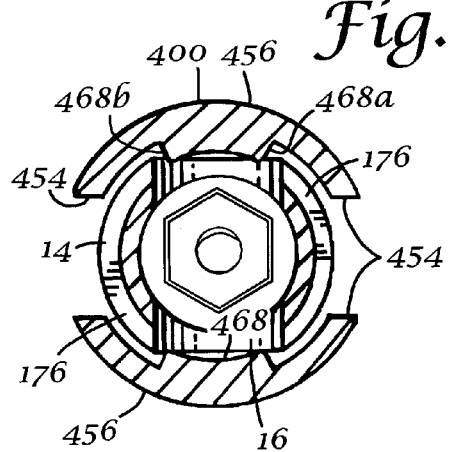
FIG. 49 is an enlarged cross-section of the assembly of FIG. 48 taken along line the 49-49 of FIG. 48 illustrating an initial step in aligning and engaging the guide tool bone screw attachment structure with the complementary bone screw tool engagement structure.
Figure 51:
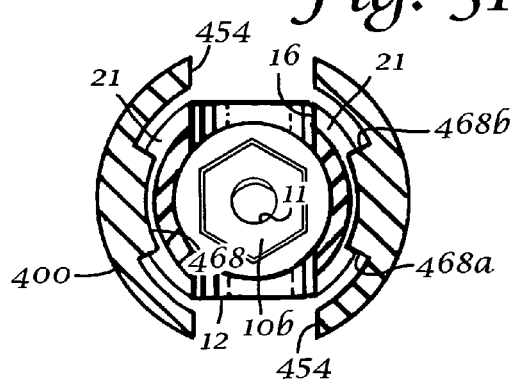
FIG. 51 is an enlarged cross-section of the guide tool and bone screw of FIG. 50 taken along line the 51-51 of FIG. 50 and showing reversible engagement between the guide tool bone screw attachment structure and the bone screw tool engagement structure.

As shown in FIGS. 47-48, the bone screw's tool engagement structure 21 is adapted to cooperate with tool's screw attachment structure 468. Accordingly, the bone screw's tool engagement structure 21 is a radial groove, slot or notch that wraps around the outer surfaces of the arms 14. The tool engagement structure 21 is oriented substantially perpendicular to the bone screw arms 14, such that it runs substantially parallel with the arm upper surfaces 15. Further, the tool engagement structures 21 are located so as to be vertically spaced very close to or adjacent to the upper surface 15. As a result, the tool's mating chamber 469 engages only a small portion of the arms 14.

Since the guide tool's bone screw attachment structure 648 and the bone screw's tool engagement structure 21 are substantially perpendicular to the longitudinal axis D of the guide tool 400, such as when the tool 400 is mounted on the bone screw 6, the guide tool 400 is rotatable in either of the clockwise and counter-clockwise directions relative to the bone screw head 12, in a twist-on procedure. Similarly, the guide tool 400 can be rotated rotatable in either of the clockwise and counter-clockwise directions in a twist-off procedure. Regardless of the direction tool rotation of the twist-on procedure, the guide tool 400 is rotated about 90-degrees relative to the bone screw head 12, so as to align the guide tool's through slot 454 with the bone screw's U-shaped channel 16, and the implantation procedure can be continued as is described above.

FIGS. 52-59 illustrate a guide tool 500 in a fifth embodiment. The fifth guide tool 500 is similar to the guide tools 1, 200, 300 and 400 of the first, second, third and fourth embodiments, the descriptions of which are incorporated herein by reference. Therefore the guide tool 500 is numbered in a manner similar to the numbering of guide tools 1, 200, 300 and 400. In particular, the guide tool 500 of the fifth embodiment includes the following structures, portions or features: a body 526 that includes an upper handle portion 528, an intermediate portion and a lower portion 532, front and back walls 536, side walls 538, top and bottom ends 540 and 542 respectively, a through-bore 544 that is coaxial with the longitudinal axis E and extends from a top opening 546 located at the top end 540 to a bottom opening 548 located at the bottom end 542. The through-bore 544 includes an inner surface 550. Cut-outs 552 in the front and back walls 536 form a through-slot 554 that extends longitudinally upward from the bottom opening 548 and is joined with the through-bore 544. The through-slot 554 also divides the lower portion 532 of the body 526 into a pair of spaced opposed legs 556. The through-slot 554 includes an upper surface 558 and openings 562. The openings 562 join the through-bore inner surface 550 with the body outer surface 560. The guide tool 500 also includes a guide and advancement structure 566 adapted for use with a closure top 22, a radially inwardly facing bone screw attachment structure 568, which is described in greater detail below, and a mating chamber 569 for engaging the bone screw 6. The mating chamber 569 includes an inner chamber surface 569a and screw abutment surfaces 569b. Similar to the guide tool 400 of the fourth embodiment, the body lower portion 532 does not include a rod-abutment relief.

Referring now to FIG. 53, a bone screw, such as but not limited to a polyaxial bone screw 6a, for use with the guide tool 500 includes a tool attachment structure 21 that is similar to that of the bone screw 6a descried with reference to FIGS. 47 through 51. For example, the tool engagement structure 21 includes a radial groove, slot or notch that wraps around the outer surface of the bone screw arms 16, such that cross-sections of the slots, which is taken perpendicular to the longitudinal axis of the head 12, are generally semi-circular, crescent-shaped or C-shaped. Additionally, the tool engagement structure 21 for use with the guide tool 500 includes a radially extending slot or notch 21e in the top surface 15 of each of the arms 14. For example, the slot 21e extends radially outward from the U-shaped channel 16 to the outer surface of the respective arm 14. As is described below, the slot 21e engages a portion of the guide tool 500, to prevent twisting of the bone screw head 12 relative to the guide tool 500, which the bone screw 6a and the guide tool 500 are engaged together. The slot 21e shown in FIG. 53 is generally shallow. However, it if foreseen that the slot 21e may be deeper than depicted, or the bone screw's tool engagement structure 21 may include additional or alternative structures.

Referring now to FIGS. 52 through 59, the guide tool 500 includes a multi-part bone screw attachment structure 568. In particular, the bone screw attachment structure 568 includes a an attachment member 568a, a ramp member 568b and a pin-receiving bore 568c. The attachment member 568a is shelf-like or shoulder-like structure located on the inner surface of the mating chamber 569, such that the attachment member 568a extends radially inwardly, toward the longitudinal axis E. The ramp member 568b is located on the exterior surface of a respective leg 556. The ramp member 568b runs parallel with the longitudinal axis E and slopes inwardly when moving from the tool upper opening 546 toward the bottom opening 548. The ramp member 568b terminates with the pin-receiving bore 568c, which is generally perpendicular to the longitudinal axis E and joins the ramp member 568b with the interior surface of the mating chamber 569. It is foreseen that the pin-receiving bore 568c may also be slopes, so as to not be perpendicular to the longitudinal axis E. The pin-receiving bore 568c is sized and shaped to receiver therein or there-through a pin or finger member of the guide tool 500, to cooperate with the slot 21e and thereby prevent rotation of the guide tool 500 with respect to the bone screw head 12, such as is described below.

The guide tool 500 also includes a tong-like sleeve member 570 that is received over the body 526 and reversibly slidable along the axis E. The sleeve member 570 includes an upper collar portion 572 with a pair of spaced opposed flex arms 574 that extend longitudinally downward from the collar portion 572. The flex arms 574 are inwardly biased. At the lower end 576 of each flex arm 574 is an inwardly extending pin or finger member 578, such as is mentioned above. The finger members 578 extend inwardly from the inner surfaces of the respective flex arms 574 along axis F.

When the sleeve member 570 is received over the guide tool body 526, the inner surfaces 580 of the flex arms 574 frictionally engage the respective outer surfaces of the legs 556. Further, each of the inwardly biased flex arms 574 flexes into respective ramp member 568b.

To mount the guide tool 500 on the bone screw head 12, the guide tool body 526 is reversibly engages with the bone screw arms 14, such as is described above with respect to the fourth guide tool 400, using a twist-on movement, such as is described above. FIG. 58 illustrates the relationship of the guide tool body 526 to the bone screw arms 14, when the two structures are reversibly engaged. In particular, the guide tool shelf member 568a is slidingly engaged in the bone screw slot 21. In some embodiments, a lip-like portion of the guide tool bottom end 542 extends downwardly on the exterior surface of a respective bone screw arm 14. It is noted, that the sleeve member is somewhat raised with respect to the guide tool body 526, such that the pins 578 are not engaged in the respective pin-receiving bores. Instead, the tips 582 of the pins 578 frictionally engage the surface of the ramp member 568.

To fully engage the guide tool's bone screw attachment structure 568 with the bone screw's tool engagement structure 21, the sleeve member 570 is slidingly moved down the body 526, such that the pins 578 are received into and through the respective pin-receiving bores 568c. The pins 578 include a length that is sufficient for them to engage the slots 21 on respective arm top surfaces 15, such as is shown in FIG. 59. When the pins 578 are engaged in the respective slots 21e, rotation of the guide tool 500 with respect to the bone screw 6a is substantially prevented.

To remove the guide tool 500 from the bone screw 6a, the sleeve member 570 is moved axially upward with respect to the body 526, such that the pins 578 are disengaged from the slots 21e. As shown in FIG. 59, the pins 578 may be somewhat conically shaped, so as to aid in this disengagement. After the pins 578 and the slots 21e have been disengaged, the guide tool body 526 may then be twisted off of the bone screw 6a, using a twist-off procedure, such as is described above.

It is to be understood that while certain forms of the present invention have been illustrated and described herein, it is not to be limited to the specific forms or arrangement of parts described and shown.

What is claimed and desired to be secured by Letters Patent is as follows:

1. A receiver for a bone anchor and comprising:
  a) a pair of laterally spaced upstanding arms having external surfaces extending from a front side to a back side of the receiver and respective upper surfaces, the arms forming a rod-receiving channel therebetween; and
  b) each arm having a laterally opening groove formed on each external surface and located near the upper surfaces, the grooves being symmetrically sized and shaped and opposed and extending radially, circumferentially, and horizontally with respect to a respective external surface, each groove extending to one of the front and back sides of the receiver.

* * * * *